US009357901B2

United States Patent
Eno et al.

(10) Patent No.: US 9,357,901 B2
(45) Date of Patent: Jun. 7, 2016

(54) METHODS AND APPARATUS FOR DISPLAYING THREE-DIMENSIONAL ORIENTATION OF A STEERABLE DISTAL TIP OF AN ENDOSCOPE

(71) Applicant: INTUITIVE SURGICAL OPERATIONS, INC., Sunnyvale, CA (US)

(72) Inventors: Robert Eno, Mountain View, CA (US); Amir Belson, Sunnyvale, CA (US); David Blaha, Sunnyvale, CA (US); David Mintz, Los Altos, CA (US); Bruce Robert Woodley, Palo Alto, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 68 days.

(21) Appl. No.: 14/039,147

(22) Filed: Sep. 27, 2013

(65) Prior Publication Data

US 2014/0094648 A1    Apr. 3, 2014

Related U.S. Application Data

(62) Division of application No. 11/750,988, filed on May 18, 2007, now Pat. No. 8,568,299.

(60) Provisional application No. 60/747,783, filed on May 19, 2006.

(51) Int. Cl.
*A61B 1/04* (2006.01)
*A61B 1/00* (2006.01)
(Continued)

(52) U.S. Cl.
CPC ............. *A61B 1/00039* (2013.01); *A61B 1/008* (2013.01); *A61B 1/00045* (2013.01); *A61B 1/0053* (2013.01); *A61B 1/0057* (2013.01); *A61B 5/7435* (2013.01); *A61B 1/0055* (2013.01)

(58) Field of Classification Search
CPC .................. A61B 1/0057; A61B 2017/00318; A61M 25/0147
USPC ......................... 600/145, 117; 604/95.04, 528
See application file for complete search history.

(56) References Cited

U.S. PATENT DOCUMENTS

| 616,672 A | 12/1898 | Kelling |
| 2,510,198 A | 6/1950 | Tesmer |

(Continued)

FOREIGN PATENT DOCUMENTS

| DE | 2823025 C2 | 2/1986 |
| DE | 3707787 A1 | 9/1988 |

(Continued)

OTHER PUBLICATIONS

Berger, W. L. et al., "Sigmoid Stiffener for Decompression Tube Placement in Colonic Pseudo-Obstruction," Endoscopy, 2000, vol. 32, Issue 1, pp. 54-57.

(Continued)

*Primary Examiner* — Anhtuan T Nguyen
*Assistant Examiner* — Rynae Boler

(57) ABSTRACT

A system for graphically visualizing an orientation of a steerable distal portion of an elongate instrument is disclosed. The system includes an instrument having an elongate body. The elongate body includes a proximal portion and a steerable distal portion. The system also includes at least one tensioning member attached to said steerable distal portion, wherein the actuation of said at least one tensioning member results in an approximate y-bend and an approximate x-bend of said steerable distal portion, and wherein said approximate y-bend and approximate x-bend define an approximate overall bend of said steerable distal portion. The system further includes a graphical user interface and an icon representing said approximate overall bend on said graphical user interface.

19 Claims, 12 Drawing Sheets

(51) Int. Cl.
 *A61B 1/005* (2006.01)
 *A61B 1/008* (2006.01)
 *A61B 5/00* (2006.01)

(56) References Cited

U.S. PATENT DOCUMENTS

| | | | |
|---|---|---|---|
| 2,533,494 A | 12/1950 | Mitchell, Jr. |
| 2,767,705 A | 10/1956 | Moore |
| 3,060,972 A | 10/1962 | Sheldon |
| 3,071,161 A | 1/1963 | Ulrich |
| 3,096,962 A | 7/1963 | Meijs |
| 3,162,214 A | 12/1964 | Wilfred, Jr. |
| 3,168,274 A | 2/1965 | Street |
| 3,190,286 A | 6/1965 | Stokes |
| 3,266,059 A | 8/1966 | Stelle |
| 3,430,662 A | 3/1969 | Guarnaschelli |
| 3,497,083 A | 2/1970 | Anderson |
| 3,546,961 A | 12/1970 | Marton |
| 3,610,231 A | 10/1971 | Takahashi et al. |
| 3,625,084 A | 12/1971 | Siebert |
| 3,643,653 A | 2/1972 | Takahashi et al. |
| 3,739,770 A | 6/1973 | Mori |
| 3,773,034 A | 11/1973 | Burns et al. |
| 3,780,740 A | 12/1973 | Rhea |
| 3,858,578 A | 1/1975 | Milo |
| 3,871,358 A | 3/1975 | Fukuda et al. |
| 3,897,775 A | 8/1975 | Furihata |
| 3,913,565 A | 10/1975 | Kawahara |
| 3,946,727 A | 3/1976 | Okada et al. |
| 3,990,434 A | 11/1976 | Free |
| 4,054,128 A | 10/1977 | Seufert et al. |
| 4,176,662 A | 12/1979 | Frazer |
| 4,233,981 A | 11/1980 | Schomacher |
| 4,236,509 A | 12/1980 | Takahashi et al. |
| 4,240,435 A | 12/1980 | Yazawa et al. |
| 4,273,111 A | 6/1981 | Tsukaya |
| 4,327,711 A | 5/1982 | Takagi |
| 4,366,810 A | 1/1983 | Slanetz, Jr. |
| 4,393,728 A | 7/1983 | Larson et al. |
| 4,432,349 A | 2/1984 | Oshiro |
| 4,483,326 A | 11/1984 | Yamaka et al. |
| 4,489,826 A | 12/1984 | Dubson |
| 4,494,417 A | 1/1985 | Larson et al. |
| 4,499,895 A | 2/1985 | Takayama |
| 4,503,842 A | 3/1985 | Takayama |
| 4,543,090 A | 9/1985 | McCoy |
| 4,551,061 A | 11/1985 | Olenick |
| 4,559,928 A | 12/1985 | Takayama |
| 4,566,843 A | 1/1986 | Iwatsuka et al. |
| 4,577,621 A | 3/1986 | Patel |
| 4,592,341 A | 6/1986 | Omagari et al. |
| 4,601,283 A | 7/1986 | Chikama |
| 4,601,713 A | 7/1986 | Fuqua |
| 4,621,618 A | 11/1986 | Omagari |
| 4,624,243 A | 11/1986 | Lowery et al. |
| 4,630,649 A | 12/1986 | Oku |
| 4,643,184 A | 2/1987 | Mobin-Uddin |
| 4,646,722 A | 3/1987 | Silverstein et al. |
| 4,648,733 A | 3/1987 | Merkt |
| 4,651,718 A | 3/1987 | Collins et al. |
| 4,655,257 A | 4/1987 | Iwashita |
| 4,683,773 A | 8/1987 | Diamond |
| 4,686,963 A | 8/1987 | Cohen et al. |
| 4,712,969 A | 12/1987 | Kimura |
| 4,726,355 A | 2/1988 | Okada |
| 4,753,222 A | 6/1988 | Morishita |
| 4,753,223 A | 6/1988 | Bremer |
| 4,754,909 A | 7/1988 | Barker et al. |
| 4,784,117 A | 11/1988 | Miyazaki |
| 4,787,369 A | 11/1988 | Allred, III et al. |
| 4,788,967 A | 12/1988 | Ueda |
| 4,793,326 A | 12/1988 | Shishido |
| 4,796,607 A | 1/1989 | Allred, III et al. |
| 4,799,474 A | 1/1989 | Ueda |
| 4,800,890 A | 1/1989 | Cramer |
| 4,807,593 A | 2/1989 | Ito |
| 4,815,450 A | 3/1989 | Patel |
| 4,832,473 A | 5/1989 | Ueda |
| 4,834,068 A | 5/1989 | Gottesman |
| 4,873,965 A | 10/1989 | Danieli |
| 4,873,990 A | 10/1989 | Holmes et al. |
| 4,879,991 A | 11/1989 | Ogiu |
| 4,884,557 A | 12/1989 | Takehana et al. |
| 4,890,602 A | 1/1990 | Hake |
| 4,895,431 A | 1/1990 | Tsujiuchi et al. |
| 4,899,731 A * | 2/1990 | Takayama et al. ............ 600/145 |
| 4,904,048 A | 2/1990 | Sogawa et al. |
| 4,917,114 A | 4/1990 | Green et al. |
| 4,919,112 A | 4/1990 | Siegmund |
| 4,930,494 A | 6/1990 | Takehana et al. |
| 4,949,927 A | 8/1990 | Madocks et al. |
| 4,957,486 A | 9/1990 | Davis |
| 4,969,709 A | 11/1990 | Sogawa et al. |
| 4,971,035 A | 11/1990 | Ito |
| 4,977,886 A | 12/1990 | Takehana et al. |
| 4,977,887 A | 12/1990 | Gouda |
| 4,987,314 A | 1/1991 | Gotanda et al. |
| 5,005,558 A | 4/1991 | Aomori |
| 5,005,559 A | 4/1991 | Blanco et al. |
| 5,014,709 A | 5/1991 | Bjelkhagen et al. |
| 5,018,509 A | 5/1991 | Suzuki et al. |
| 5,025,778 A | 6/1991 | Silverstein et al. |
| 5,060,632 A | 10/1991 | Hibino et al. |
| 5,092,901 A | 3/1992 | Hunter et al. |
| 5,125,395 A | 6/1992 | Adair |
| 5,127,393 A | 7/1992 | McFarlin et al. |
| 5,159,446 A | 10/1992 | Hibino et al. |
| 5,166,787 A | 11/1992 | Irion |
| 5,174,276 A | 12/1992 | Crockard |
| 5,174,277 A | 12/1992 | Matsumaru |
| 5,188,111 A | 2/1993 | Yates et al. |
| 5,207,695 A | 5/1993 | Trout, III |
| 5,217,001 A | 6/1993 | Nakao et al. |
| 5,220,911 A | 6/1993 | Tamura |
| 5,228,429 A | 7/1993 | Hatano |
| 5,234,448 A | 8/1993 | Wholey et al. |
| 5,243,967 A | 9/1993 | Hibino |
| 5,250,058 A | 10/1993 | Miller et al. |
| 5,251,611 A | 10/1993 | Zehel et al. |
| 5,253,647 A | 10/1993 | Takahashi et al. |
| 5,254,809 A | 10/1993 | Martin |
| 5,257,617 A | 11/1993 | Takahashi |
| 5,259,364 A | 11/1993 | Bob et al. |
| 5,271,381 A | 12/1993 | Ailinger et al. |
| 5,271,382 A | 12/1993 | Chikama |
| 5,279,610 A | 1/1994 | Park et al. |
| 5,297,443 A | 3/1994 | Wentz |
| 5,325,845 A | 7/1994 | Adair |
| 5,337,732 A | 8/1994 | Grundfest et al. |
| 5,337,733 A | 8/1994 | Bauerfeind et al. |
| 5,343,874 A | 9/1994 | Picha et al. |
| 5,347,987 A | 9/1994 | Feldstein et al. |
| 5,348,259 A | 9/1994 | Blanco et al. |
| 5,370,108 A | 12/1994 | Miura et al. |
| 5,383,467 A | 1/1995 | Auer et al. |
| 5,383,852 A | 1/1995 | Stevens-Wright |
| 5,389,222 A | 2/1995 | Shahinpoor |
| 5,394,864 A | 3/1995 | Kobayashi et al. |
| 5,400,769 A | 3/1995 | Tanii et al. |
| 5,402,768 A | 4/1995 | Adair |
| 5,411,508 A | 5/1995 | Bessler et al. |
| 5,413,108 A | 5/1995 | Alfano |
| 5,421,337 A | 6/1995 | Richards-Kortum et al. |
| 5,425,738 A | 6/1995 | Gustafson et al. |
| 5,429,118 A | 7/1995 | Cole et al. |
| 5,439,000 A | 8/1995 | Gunderson et al. |
| 5,451,221 A | 9/1995 | Cho et al. |
| 5,456,714 A | 10/1995 | Owen |
| 5,460,166 A | 10/1995 | Yabe et al. |
| 5,460,168 A | 10/1995 | Masubuchi et al. |
| 5,469,840 A | 11/1995 | Tanii et al. |
| 5,482,029 A | 1/1996 | Sekiguchi et al. |
| 5,487,757 A | 1/1996 | Truckai et al. |
| 5,489,256 A | 2/1996 | Adair |

(56) References Cited

U.S. PATENT DOCUMENTS

| | | |
|---|---|---|
| 5,507,287 A | 4/1996 | Palcic et al. |
| 5,507,717 A | 4/1996 | Kura et al. |
| 5,531,664 A | 7/1996 | Adachi et al. |
| 5,551,945 A | 9/1996 | Yabe et al. |
| 5,558,619 A | 9/1996 | Kami et al. |
| 5,558,665 A | 9/1996 | Kieturakis |
| 5,577,992 A | 11/1996 | Chiba et al. |
| 5,586,968 A | 12/1996 | Grundl et al. |
| 5,590,660 A | 1/1997 | MacAulay et al. |
| 5,601,087 A | 2/1997 | Gunderson et al. |
| 5,602,449 A | 2/1997 | Krause et al. |
| 5,620,408 A | 4/1997 | Vennes et al. |
| 5,624,380 A | 4/1997 | Takayama et al. |
| 5,624,381 A | 4/1997 | Kieturakis |
| 5,626,553 A | 5/1997 | Frassica et al. |
| 5,645,520 A | 7/1997 | Nakamura et al. |
| 5,647,368 A | 7/1997 | Zeng et al. |
| 5,651,769 A | 7/1997 | Waxman et al. |
| 5,653,690 A | 8/1997 | Booth et al. |
| 5,658,238 A | 8/1997 | Suzuki et al. |
| 5,662,585 A | 9/1997 | Willis et al. |
| 5,662,587 A | 9/1997 | Grundfest et al. |
| 5,665,050 A | 9/1997 | Benecke |
| 5,667,476 A | 9/1997 | Frassica et al. |
| 5,679,216 A | 10/1997 | Takayama et al. |
| 5,728,044 A | 3/1998 | Shan |
| 5,733,245 A | 3/1998 | Kawano |
| 5,749,828 A | 5/1998 | Solomon et al. |
| 5,752,912 A | 5/1998 | Takahashi et al. |
| 5,759,151 A | 6/1998 | Sturges |
| 5,762,613 A | 6/1998 | Sutton et al. |
| 5,765,561 A | 6/1998 | Chen et al. |
| 5,769,792 A | 6/1998 | Palcic et al. |
| 5,772,597 A | 6/1998 | Goldberger et al. |
| 5,773,835 A | 6/1998 | Sinofsky |
| 5,779,624 A | 7/1998 | Chang |
| 5,807,241 A | 9/1998 | Heimberger |
| 5,810,715 A | 9/1998 | Moriyama |
| 5,810,716 A | 9/1998 | Mukherjee et al. |
| 5,810,717 A | 9/1998 | Maeda et al. |
| 5,810,776 A | 9/1998 | Bacich et al. |
| 5,813,976 A | 9/1998 | Filipi et al. |
| 5,827,190 A | 10/1998 | Palcic et al. |
| 5,842,973 A | 12/1998 | Bullard |
| 5,860,581 A | 1/1999 | Robertson et al. |
| 5,860,914 A | 1/1999 | Chiba et al. |
| 5,876,329 A | 3/1999 | Harhen |
| 5,876,373 A | 3/1999 | Giba et al. |
| 5,885,208 A | 3/1999 | Moriyama |
| 5,893,369 A | 4/1999 | Lemole |
| 5,897,417 A | 4/1999 | Grey |
| 5,897,488 A | 4/1999 | Ueda |
| 5,902,254 A | 5/1999 | Magram |
| 5,906,591 A | 5/1999 | Dario et al. |
| 5,908,381 A | 6/1999 | Aznoian et al. |
| 5,912,147 A | 6/1999 | Stoler et al. |
| 5,916,147 A | 6/1999 | Boury |
| 5,921,915 A | 7/1999 | Aznoian et al. |
| 5,928,136 A | 7/1999 | Barry |
| 5,941,815 A | 8/1999 | Chang |
| 5,941,908 A | 8/1999 | Goldsteen et al. |
| 5,957,833 A | 9/1999 | Shan |
| 5,968,052 A | 10/1999 | Sullivan, III |
| 5,971,767 A | 10/1999 | Kaufman et al. |
| 5,976,074 A | 11/1999 | Moriyama |
| 5,982,377 A | 11/1999 | Yamashita et al. |
| 5,989,182 A | 11/1999 | Hori et al. |
| 5,989,230 A | 11/1999 | Frassica |
| 5,993,381 A | 11/1999 | Ito |
| 5,993,447 A | 11/1999 | Blewett et al. |
| 5,996,346 A | 12/1999 | Maynard |
| 6,016,440 A | 1/2000 | Simon et al. |
| 6,033,359 A | 3/2000 | Doi |
| 6,036,636 A | 3/2000 | Motoki et al. |
| 6,042,155 A | 3/2000 | Lockwood |
| 6,048,307 A | 4/2000 | Grundl et al. |
| 6,063,022 A | 5/2000 | Ben-Haim |
| 6,066,102 A | 5/2000 | Townsend et al. |
| 6,066,132 A | 5/2000 | Chen et al. |
| 6,068,638 A | 5/2000 | Makower |
| 6,096,289 A | 8/2000 | Goldenberg |
| 6,099,464 A | 8/2000 | Shimizu et al. |
| 6,099,465 A | 8/2000 | Inoue |
| 6,099,485 A | 8/2000 | Patterson |
| 6,106,510 A | 8/2000 | Lunn et al. |
| 6,119,913 A | 9/2000 | Adams et al. |
| 6,129,667 A | 10/2000 | Dumoulin et al. |
| 6,129,683 A | 10/2000 | Sutton et al. |
| 6,141,577 A | 10/2000 | Rolland et al. |
| 6,149,581 A | 11/2000 | Klingenstein |
| 6,162,171 A | 12/2000 | Ng et al. |
| 6,174,280 B1 | 1/2001 | Oneda et al. |
| 6,174,291 B1 | 1/2001 | McMahon et al. |
| 6,179,776 B1 | 1/2001 | Adams et al. |
| 6,185,448 B1 | 2/2001 | Borovsky |
| 6,201,989 B1 | 3/2001 | Whitehead et al. |
| 6,203,493 B1 | 3/2001 | Ben-Haim |
| 6,203,494 B1 | 3/2001 | Moriyama |
| 6,210,337 B1 | 4/2001 | Dunham et al. |
| 6,221,006 B1 | 4/2001 | Dubrul et al. |
| 6,241,657 B1 | 6/2001 | Chen et al. |
| 6,249,076 B1 | 6/2001 | Madden et al. |
| 6,270,453 B1 | 8/2001 | Sakai |
| 6,306,081 B1 | 10/2001 | Ishikawa et al. |
| 6,309,346 B1 | 10/2001 | Farhadi |
| 6,315,714 B1 | 11/2001 | Akiba |
| 6,319,197 B1 | 11/2001 | Tsuji et al. |
| 6,327,492 B1 | 12/2001 | Lemelson |
| 6,332,089 B1 | 12/2001 | Acker et al. |
| 6,348,058 B1 | 2/2002 | Melkent et al. |
| 6,366,799 B1 | 4/2002 | Acker et al. |
| 6,402,687 B1 | 6/2002 | Ouchi |
| 6,408,889 B1 | 6/2002 | Komachi |
| 6,428,203 B1 | 8/2002 | Danley |
| 6,432,041 B1 * | 8/2002 | Taniguchi et al. ............ 600/118 |
| 6,443,888 B1 | 9/2002 | Ogura et al. |
| 6,453,190 B1 | 9/2002 | Acker et al. |
| 6,459,481 B1 | 10/2002 | Schaack |
| 6,468,203 B2 | 10/2002 | Belson |
| 6,482,149 B1 | 11/2002 | Torii |
| 6,485,413 B1 | 11/2002 | Boppart et al. |
| 6,490,467 B1 | 12/2002 | Bucholz et al. |
| 6,511,417 B1 | 1/2003 | Taniguchi et al. |
| 6,511,418 B2 | 1/2003 | Shahidi et al. |
| 6,517,477 B1 | 2/2003 | Wendlandt |
| 6,527,706 B2 | 3/2003 | Ide |
| 6,537,211 B1 | 3/2003 | Wang et al. |
| 6,544,215 B1 | 4/2003 | Bencini et al. |
| 6,554,793 B1 | 4/2003 | Pauker et al. |
| 6,569,173 B1 | 5/2003 | Blatter et al. |
| 6,616,600 B2 | 9/2003 | Pauker |
| 6,638,213 B2 | 10/2003 | Ogura et al. |
| 6,641,528 B2 | 11/2003 | Torii |
| 6,656,110 B1 | 12/2003 | Irion et al. |
| 6,699,183 B1 | 3/2004 | Wimmer |
| 6,761,685 B2 | 7/2004 | Adams et al. |
| 6,773,393 B1 * | 8/2004 | Taniguchi et al. ............ 600/117 |
| 6,783,491 B2 | 8/2004 | Saadat et al. |
| 6,790,173 B2 | 9/2004 | Saadat et al. |
| 6,800,056 B2 | 10/2004 | Tartaglia et al. |
| 6,808,499 B1 | 10/2004 | Churchill et al. |
| 6,808,520 B1 | 10/2004 | Fourkas et al. |
| 6,817,973 B2 | 11/2004 | Merril et al. |
| 6,837,846 B2 | 1/2005 | Jaffe et al. |
| 6,837,847 B2 | 1/2005 | Ewers et al. |
| 6,837,849 B2 | 1/2005 | Ogura et al. |
| 6,843,793 B2 | 1/2005 | Brock et al. |
| 6,850,794 B2 | 2/2005 | Shahidi |
| 6,858,005 B2 | 2/2005 | Ohline et al. |
| 6,869,396 B2 | 3/2005 | Belson |
| 6,875,170 B2 | 4/2005 | Francois et al. |
| 6,890,297 B2 | 5/2005 | Belson |
| 6,902,528 B1 | 6/2005 | Garibaldi et al. |
| 6,942,613 B2 | 9/2005 | Ewers et al. |

(56) References Cited

U.S. PATENT DOCUMENTS

| | | |
|---|---|---|
| 6,960,161 B2 | 11/2005 | Amling et al. |
| 6,960,162 B2 | 11/2005 | Saadat et al. |
| 6,960,163 B2 | 11/2005 | Ewers et al. |
| 6,974,411 B2 | 12/2005 | Belson |
| 6,984,203 B2 | 1/2006 | Tartaglia et al. |
| 7,018,331 B2 | 3/2006 | Chang et al. |
| 7,041,053 B2 | 5/2006 | Miyake |
| 7,087,013 B2 | 8/2006 | Belson et al. |
| 8,182,418 B2 | 5/2012 | Durant et al. |
| 8,568,299 B2 | 10/2013 | Eno et al. |
| 2002/0016607 A1 | 2/2002 | Bonadio et al. |
| 2002/0062062 A1 | 5/2002 | Belson et al. |
| 2002/0120254 A1 | 8/2002 | Julian et al. |
| 2002/0147385 A1 | 10/2002 | Butler et al. |
| 2002/0151767 A1 | 10/2002 | Sonnenschein et al. |
| 2002/0169361 A1 | 11/2002 | Taniguchi et al. |
| 2002/0188174 A1 | 12/2002 | Aizawa et al. |
| 2002/0193662 A1 | 12/2002 | Belson |
| 2003/0083550 A1 | 5/2003 | Miyagi |
| 2003/0130598 A1 | 7/2003 | Manning et al. |
| 2003/0167007 A1 | 9/2003 | Belson |
| 2003/0182091 A1 | 9/2003 | Kukuk |
| 2003/0195387 A1 | 10/2003 | Kortenbach et al. |
| 2003/0233056 A1 | 12/2003 | Saadat et al. |
| 2003/0236505 A1 | 12/2003 | Bonadio et al. |
| 2003/0236549 A1 | 12/2003 | Bonadio et al. |
| 2004/0019254 A1 | 1/2004 | Belson et al. |
| 2004/0044270 A1 | 3/2004 | Barry |
| 2004/0049251 A1 | 3/2004 | Knowlton |
| 2004/0097788 A1 | 5/2004 | Mourlas et al. |
| 2004/0106852 A1 | 6/2004 | Windheuser et al. |
| 2004/0176683 A1 | 9/2004 | Whitin et al. |
| 2004/0186350 A1 | 9/2004 | Brenneman et al. |
| 2004/0193008 A1 | 9/2004 | Jaffe et al. |
| 2004/0193009 A1 | 9/2004 | Jaffe et al. |
| 2004/0210109 A1 | 10/2004 | Jaffe et al. |
| 2004/0220450 A1 | 11/2004 | Jaffe et al. |
| 2004/0230096 A1 | 11/2004 | Stefanchik et al. |
| 2005/0020901 A1 | 1/2005 | Belson et al. |
| 2005/0065435 A1* | 3/2005 | Rauch et al. ............... 600/427 |
| 2005/0085693 A1 | 4/2005 | Belson et al. |
| 2005/0124855 A1 | 6/2005 | Jaffe et al. |
| 2005/0137454 A1 | 6/2005 | Saadat et al. |
| 2005/0137455 A1 | 6/2005 | Ewers et al. |
| 2005/0137456 A1 | 6/2005 | Saadat et al. |
| 2005/0154258 A1 | 7/2005 | Tartaglia et al. |
| 2005/0154261 A1 | 7/2005 | Ohline et al. |
| 2005/0165276 A1 | 7/2005 | Belson et al. |
| 2005/0168571 A1 | 8/2005 | Lia et al. |
| 2005/0203339 A1 | 9/2005 | Butler et al. |
| 2005/0209506 A1 | 9/2005 | Butler et al. |
| 2005/0209509 A1 | 9/2005 | Belson |
| 2005/0222497 A1 | 10/2005 | Belson |
| 2005/0222498 A1 | 10/2005 | Belson |
| 2005/0250990 A1 | 11/2005 | Le et al. |
| 2006/0009678 A1 | 1/2006 | Jaffe et al. |
| 2006/0052664 A1 | 3/2006 | Julian et al. |
| 2006/0235457 A1 | 10/2006 | Belson |
| 2006/0235458 A1 | 10/2006 | Belson |
| 2006/0258912 A1 | 11/2006 | Belson et al. |
| 2007/0043259 A1 | 2/2007 | Jaffe et al. |
| 2007/0093858 A1 | 4/2007 | Gambale et al. |
| 2007/0135803 A1 | 6/2007 | Belson |
| 2007/0161291 A1 | 7/2007 | Swinehart et al. |
| 2007/0161857 A1 | 7/2007 | Durant et al. |
| 2007/0249901 A1 | 10/2007 | Ohline et al. |
| 2008/0045794 A1 | 2/2008 | Belson |
| 2008/0154288 A1 | 6/2008 | Belson |
| 2009/0099420 A1 | 4/2009 | Woodley et al. |

FOREIGN PATENT DOCUMENTS

| | | |
|---|---|---|
| DE | 4102211 A1 | 8/1991 |
| DE | 19626433 A1 | 1/1998 |
| DE | 19729499 A1 | 1/1999 |
| EP | 165718 A2 | 12/1985 |
| EP | 382974 A1 | 8/1990 |
| EP | 497781 B1 | 1/1994 |
| EP | 0993804 A1 | 4/2000 |
| EP | 1101442 A2 | 5/2001 |
| EP | 1681013 A1 | 7/2006 |
| FR | 2732225 A1 | 10/1996 |
| GB | 2347685 A | 9/2000 |
| IE | 20000559 | 7/2000 |
| IE | 20020170 | 3/2002 |
| JP | 63136014 A2 | 6/1988 |
| JP | 63272322 A2 | 11/1988 |
| JP | 1152413 A2 | 6/1989 |
| JP | 1229220 A2 | 9/1989 |
| JP | 1262372 A2 | 10/1989 |
| JP | 2246986 A2 | 10/1990 |
| JP | 2296209 A2 | 12/1990 |
| JP | 3136630 A2 | 6/1991 |
| JP | 4054970 A2 | 2/1992 |
| JP | 5011196 A2 | 1/1993 |
| JP | 5111458 A2 | 5/1993 |
| JP | 5305073 A2 | 11/1993 |
| JP | 6007287 A2 | 1/1994 |
| JP | 8322786 A2 | 12/1996 |
| JP | 9028662 A2 | 2/1997 |
| JP | 10337274 A2 | 12/1998 |
| JP | 11042258 A2 | 2/1999 |
| JP | 21046318 A2 | 2/2001 |
| SU | 871786 A1 | 10/1981 |
| SU | 1256955 A1 | 9/1986 |
| SU | 1301701 A1 | 4/1987 |
| WO | WO-9317751 A1 | 9/1993 |
| WO | WO-9419051 A1 | 9/1994 |
| WO | WO-9504556 A2 | 2/1995 |
| WO | WO-9509562 A1 | 4/1995 |
| WO | WO-9605768 A1 | 2/1996 |
| WO | WO-9710746 A1 | 3/1997 |
| WO | WO-9725101 A2 | 7/1997 |
| WO | WO-9729701 A1 | 8/1997 |
| WO | WO-9729710 A1 | 8/1997 |
| WO | WO-9824017 A2 | 6/1998 |
| WO | WO-9849938 A1 | 11/1998 |
| WO | WO-9916359 A1 | 4/1999 |
| WO | WO-9933392 A1 | 7/1999 |
| WO | WO-9951283 A2 | 10/1999 |
| WO | WO-9959664 A1 | 11/1999 |
| WO | WO-0010456 A1 | 3/2000 |
| WO | WO-0027462 A1 | 5/2000 |
| WO | WO-0054653 A1 | 9/2000 |
| WO | WO-0074565 A1 | 12/2000 |
| WO | WO-0149353 A2 | 7/2001 |
| WO | WO-0167964 A2 | 9/2001 |
| WO | WO-0170096 A1 | 9/2001 |
| WO | WO-0170097 A1 | 9/2001 |
| WO | WO-0174235 A1 | 10/2001 |
| WO | WO-0180935 A1 | 11/2001 |
| WO | WO-0224058 A2 | 3/2002 |
| WO | WO-0239909 A1 | 5/2002 |
| WO | WO-0247549 A1 | 6/2002 |
| WO | WO-02064028 A1 | 8/2002 |
| WO | WO-02068988 A1 | 9/2002 |
| WO | WO-02069841 A2 | 9/2002 |
| WO | WO-02089692 A1 | 11/2002 |
| WO | WO-02096276 A1 | 12/2002 |
| WO | WO-03028547 A2 | 4/2003 |
| WO | WO-0373921 A1 | 9/2003 |
| WO | WO-03073920 A2 | 9/2003 |
| WO | WO-03092476 A2 | 11/2003 |
| WO | WO-2004006980 A2 | 1/2004 |
| WO | WO-2004019769 A1 | 3/2004 |
| WO | WO-2004049905 A2 | 6/2004 |
| WO | WO-2004071284 A1 | 8/2004 |
| WO | WO-2004080313 A1 | 9/2004 |
| WO | WO-2004084702 A2 | 10/2004 |

(56) References Cited

FOREIGN PATENT DOCUMENTS

| WO | WO-2005084542 A1 | 9/2005 |
|---|---|---|
| WO | WO-2006134881 A1 | 12/2006 |

OTHER PUBLICATIONS

Hasson, H.M., "Technique of Open Laparoscopy," (from step 1 to step 9), May 1979, 2424 North Clark Street, Chicago, Illinois 60614, 3 pages.

International Search Report and Written Opinion for Application No. PCT/US2007/069315, mailed on Mar. 3, 2008, 7 pages.

Ireland Application No. 2000/0225 filed on Mar. 22, 2000, Inventor Declan B., et al.

Laptop Magazine, Science & Technology section, Oct. 2002, pp. 98, 100, and 102.

Lee, Thomas S. et al., "A highly redundant robot system for inspection," Proceedings of Conference on Intelligent Robotics in Field, Factory, Service, and Space (CIRFFSS '94). Mar. 21-24, 1994. vol. 1, pp. 142-148. Houston, Texas.

McKernan, J.B. et al., "Laparoscopic general surgery," Journal of the Medical Association of Georgia, Mar. 1990, vol. 79, Issue 3, pp. 157-159.

Slatkin, A.B. et al., "The development of a robotic endoscope," Proceedings 1995 IEEE/RSJ International Conference on Intelligent Robots and Systems, Aug. 5-9, 1995, vol. 2, pp. 162-171, Pittsburgh, Pennsylvania.

Vertut, Jean and Phillipe Coiffet, Robot Technology: Teleoperation and Robotics Evolution and Development, English translation, Prentice-Hall, Inc., Inglewood Cliffs, NJ, USA, 1986, vol. 3A, 332 pages.

\* cited by examiner

METHODS AND APPARATUS FOR DISPLAYING THREE-DIMENSIONAL ORIENTATION OF A STEERABLE DISTAL TIP OF AN ENDOSCOPE

CROSS REFERENCE TO RELATED APPLICATIONS

This application is a divisional of U.S. patent application Ser. No. 11/750,988 (filed on May 18, 2007; currently pending), which claims the benefit of priority of U.S. Provisional Patent Application No. 60/747,783 (filed on May 19, 2006), each of which is incorporated herein by reference in its entirety.

INCORPORATION BY REFERENCE

All publications and patent applications mentioned in this specification are incorporated herein by reference in their entirety to the same extent as if each individual publication or patent application was specifically and individually indicated to be incorporated by reference.

FIELD OF INVENTION

The present invention relates, generally, to reporting the approximate three-dimensional orientation of the steerable distal portion of an endoscope to the user of the endoscope. More particularly, the present invention relates to a system and method for providing the endoscope-user a display from which to more easily determine the approximate three-dimensional orientation of the steerable distal portion of the endoscope, thereby facilitating navigation of the endoscope. The present invention also relates to a system and method for limiting the amount the steerable distal portion can bend overall to reduce or eliminate the user's ability to bend the steerable distal portion of the endoscope beyond a preset amount.

BACKGROUND OF THE INVENTION

An endoscope is an elongated instrument used in both medical and industrial applications for visualizing and operating on hard to reach areas such as, without limitation, a lumen within a body or an industrial pipe. With regard to medical applications, endoscopes can be used for a variety of different diagnostic and interventional procedures, including colonoscopy, upper GI endoscopy, bronchoscopy, thoracoscopy, laparoscopy and video endoscopy.

Colonoscopy, as one example for use of an endoscope, is a medical procedure in which a flexible endoscope, or colonoscope, is inserted into a patient's colon for diagnostic examination and/or surgical treatment of the colon. A standard colonoscope is typical 135-185 cm in length and 12-19 mm in diameter, and includes a fiber optic imaging bundle or a miniature camera located at the instrument's tip, illumination fibers, one or two instrument channels that may also be used for insufflation or irrigation, air and water channels, and vacuum channels. The colonoscope is usually inserted via the patient's anus and advanced through the colon, allowing direct visual examination of the colon, the ileocecal valve and portions of the terminal ileum. Insertion of the colonoscope is complicated by the fact that the colon represents a tortuous and convoluted path. Considerable manipulation of the colonoscope is often necessary to advance the colonoscope through the colon, making the procedure more difficult and time consuming and adding to the potential for complication, such as intestinal perforation.

Steerable colonoscopes have been devised to facilitate selection of the correct path through the curves of the colon. However, as the colonoscope is inserted further and further into the colon, it becomes more difficult to advance the colonoscope along the selected path. At each turn, the wall of the colon must maintain the curve in the colonoscope. The colonoscope rubs against the mucosal surface of the colon along the outside of each turn. Friction and slack in the colonoscope build up at each turn, making it more and more difficult to advance and withdraw the colonoscope. In addition, the force against the wall of the colon increases with the buildup of friction. In cases of extreme tortuosity, it may become impossible to advance the colonoscope all the way through the colon.

Through a visual imaging device on the distal tip of the colonoscope, the user can observe images transmitted from the distal end of the colonoscope. It is primarily from these images and from the user's general knowledge of the colon's basic anatomical shape that a user attempts to guide the colonoscope through the tortuous path of the colon. Despite her knowledge, skill and best efforts the user can become very disoriented within the three-dimensional space of the colon with only a camera to visualize and orient the steerable distal tip of the colonoscope. For example the user may need to remove a polyp and have a difficult time reorienting herself as to which way is forward; the user may have caused the camera to rotate in space, for example by "torqueing" the proximal end of the scope, and this alone or in combination with bending the steerable distal tip can also result in a loss of orientation. A loss of orientation frequently requires the user to withdraw the colonoscope a certain distance to re-orientate the user. Reorientation of the user results in increased procedure time, which increases patient discomfort and increases the amount of time spent treating the patient with concomitant loss of throughput and revenue for an endoscopic treatment center.

SUMMARY OF THE INVENTION

Information about the approximate, real-time three-dimensional orientation of a steerable distal portion of an endoscope will aid a user, medical or industrial, to re-orient the user within the remote three-dimensional space through which the endoscope is being advanced. Typically, an endoscope comprises an elongate body with a steerable distal portion and a flexible portion proximal to the steerable distal portion. Olympus, Fujinon, and Pentax and others manufacture and sell scopes with the passive flexible portion proximal to the steerable distal portion. In more advanced scopes, such as those currently under investigation and development by NeoGuide Systems, Inc., the flexible portion proximal to the steerable distal portion undergoes automatic control by a controller or computer such that the flexible proximal portion assumes and maintains the curvature of the segment preceding it as the endoscope is advanced into the remote three-dimensional space under the investigation. These latter endoscopes are more fully described in granted patents and co-pending applications each having a common assignee to that of the present application: U.S. Pat. No. 6,468,203; U.S. patent application Ser. No. 09/969,927 filed Oct. 2, 1001; U.S. patent application Ser. No. 10/229,577 file Aug. 27, 2002; Ser. No. 10/087,100 filed Mar. 1, 2002; and U.S. patent application Ser. No. 10/139,289 filed May 2, 2002, each of which has been incorporated by reference into the present application above.

One embodiment of the present invention provides a system for graphically visualizing an approximate three-dimensional orientation of a steerable distal portion of an elongate instrument in approximate real time. The system of this embodiment comprises an instrument having an elongate body, the elongate body having a proximal portion and a steerable distal portion. There is also a plurality of tensioning members connected to the steerable distal portion, wherein actuation of the tensioning members independently causes the steerable distal portion to have an approximate y-bend and an approximate x-bend. The combination of the approximate y-bend and the approximate x-bend results in an overall bend of the steerable distal portion of the endoscope. The overall bend is the approximate degree by which the steerable distal portion bends relative to a longitudinal axis of a proximal reference frame. This embodiment of the invention also includes a graphical user interface for displaying an icon representing the approximate overall bend and the approximate y-bend and the approximate x-bend. In particular the icon of this embodiment is a dot representing a vector diagram. The magnitude of the vector from the origin of the graphical user interface to the icon represents the degree of overall bend of the steerable distal portion. The direction of the vector from the origin of the graphical user interface is the approximate direction of the steerable distal section relative to an x-y reference frame.

Another embodiment of the present invention is a method for graphically visualizing, in approximate real time, an approximate three-dimensional orientation of a steerable distal portion of an elongate instrument. The instrument, an endoscope or colonoscope for example and without limitation, has a plurality of tensioning members attached to the steerable distal portion. The method of this embodiment comprises actuating at least one of the tensioning members to result in an approximate y-bend and an approximate x-bend of said steerable distal portion. The combination of the approximate y-bend and the approximate x-bend results in an overall bend of the steerable distal portion of the endoscope. The overall bend is the approximate degree by which the steerable distal portion bends relative to a proximal reference frame. The method of this embodiment also comprises displaying on a graphical user interface, in approximate real time, an icon representing an approximate orientation of said steerable distal portion. A cross-hair graphical user interface may also be provided, in which the cross-hair represents a y- and x-axis coordinate reference frame located somewhere along and perpendicular to the longitudinal axis of the steerable distal portion when in its approximate straight configuration. In particular the icon of this embodiment is a dot representing a vector diagram. The magnitude of the vector from the origin the user interface to the icon represents the degree of overall bend of the steerable distal portion. The direction of the vector from the origin of the user interface is the approximate direction of the steerable distal section relative to an x-y reference frame along the longitudinal axis, preferably at the most proximal joint segment, of the steerable distal portion when the steerable distal portion is at the most proximal joint segment, of the steerable distal portion is at the approximate straight ahead position.

The embodiments of the present invention may also include that the cross-hair extends through the approximate center of a plurality of concentric circles. Thus, the distance from the center of the cross-hair (also the approximate center of the concentric circles) to each of the circles represents the approximate degree of the overall bend, i.e., the magnitude of the vector measured from the approximate center of the concentric circles. The direction of the vector from the origin of the graphical user interface is the approximate direction of the steerable distal section relative to the x-y reference frame along the longitudinal axis of the steerable distal portion when the steerable distal portion is at the approximate straight ahead position.

BRIEF DESCRIPTION OF THE DRAWINGS

The novel features of the invention are set forth with particularity in the claims that follow. A better understanding of the features and advantages of the present invention will be obtained by reference to the detailed description below that sets forth illustrative embodiments, in which the principles of the invention are utilized, and the accompanying drawings.

In the drawings.

DETAILED DESCRIPTION OF THE INVENTION

Figure 1:
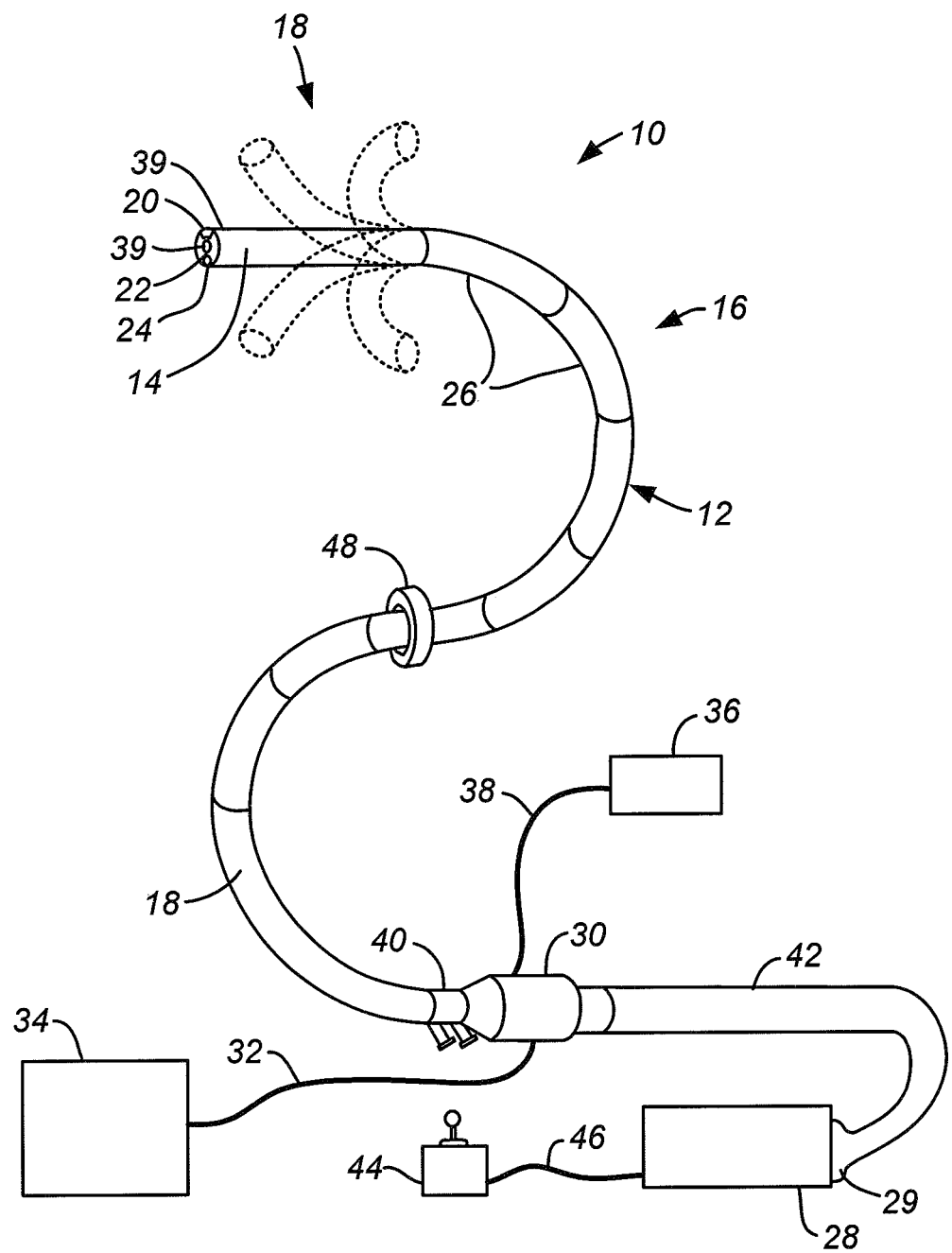
FIG. 1 depicts an endoscope in accordance with an embodiment of the present invention.

FIG. 1 depicts endoscope 10, a colonoscope in particular, in accordance with an embodiment of the present invention. Endoscope 10 has elongate body 12 with steerable distal portion 14, automatically controlled proximal portion 16, and flexible and passively manipulation proximal portion 18. The skilled artisan will appreciate that automatically controlled proximal portion 16 and flexible and passively manipulated proximal portion 18 may both be flexible and passively manipulated, although it is preferred to provide automatically controlled proximal portion 16. The skilled artisan will also appreciate that elongate body 12 can have only steerable distal portion 14 and automatically controlled portion 16. Steerable distal portion 14 can be articulated manually by turning knobs as with endoscopes produced, for example, by Olympus, or by an actuator as described below and more thoroughly in, for example, U.S. patent application Ser. No. 10/229,577 previously incorporated herein by reference.

Selectively steerable distal portion 14 can be selectively bent in any direction 18, as will be more thoroughly described later. Fiber optic imaging bundle 20 and illumination fiber(s) 22 may extend through body 12 from automatically controlled proximal portion 16 to steerable distal portion 14. Alternatively, endoscope 10 may be configured as a video endoscope with video camera 24 (e.g., CCD or CMOS camera), positioned at the distal end of steerable distal portion 14. As the skilled artisan appreciates, a user views live or delayed video feed from video camera 24 via a video cable (e.g., wire or optical fiber, not shown) or through wireless transmission of the video signal. Typically, as will be appreciated by the skilled artisan, endoscope 10 will also include one or more access lumens, working channels, light channels, air and water channels, vacuum channels, and a host of other well known complements useful for both medical and industrial endoscopy. These channels and other amenities are shown generically as 39, because such channels and amenities are well known and appreciated by the skilled artisan.

When present, automatically controlled proximal portion 16 comprises at least one segment 26, and preferably several such segments 26, which are controlled via computer and/or electronic controller 28. Each segment 26 has tendons mechanically connected to actuators as more fully described in U.S. patent application Ser. No. 10/299,577, previously incorporated herein by reference. Steerable distal portion 14 also has tendons mechanically connected to joint-segments in the steerable distal portion 14, as more thoroughly discussed below and in U.S. patent application Ser. No. 10/229,577 previously incorporated herein. The actuators driving the tendons may include a variety of different types of mechanisms capable of applying a force to a tendon, e.g., electromechanical motors, pneumatic and hydraulic cylinders, pneumatic and hydraulic motors solenoids, shape memory alloy wires, electronic rotary actuators or other devices or methods as known in the art. If shape memory alloy wires are used, they are preferably configured into several wire bundles attached at a proximal end of each of the tendons within the controller. Segment articulation may be accomplished by applying energy, e.g., electrical current, electrical voltage, heat, etc., to each of the bundles to actuate a linear motion in the wire bundles which in turn actuate the tendon movement. The linear translation of the actuators within the controller may be configured to move over a relatively short distance to accomplish effective articulation depending upon the desired degree of segment movement and articulation.

Handle 30 may be attached to the proximal end of endoscope 10. Handle 30 may include an ocular connected to fiberoptic imaging bundle 20 for direct viewing. Handle 30 may otherwise have connector 32 for connection to a video monitor, camera, e.g., a CCD or CMOS camera, or recording device 34. Handle 30 may be connected to illumination source 36 by illumination cable 38 that is connected to or continuous with the illumination fibers 22. Alternatively, some or all of these connections could be made at electronic controller 28. Luer lock fittings 40 may be located on handle 30 and connected to the various instrument channels.

Handle 30 may be connected to electronic controller 28 by way of controller cable 42. Steering controller 44 may be connected to electronic controller 28 by way of second cable 46 or it may optionally be connected directly to handle 30. Alternatively, handle 30 may have steering controller 44 integrated directly into the handle, e.g., in the form of a joystick, conventional disk controllers such as dials, pulleys or wheels, etc. Steering controller 44 allows the user to selectively steer or bend steerable distal portion 14 of elongate body 12 in the desired direction 18. Steering controller 44 may be a joystick controller as shown, or other steering control mechanism, e.g., dual dials or rotary knobs as in conventional endoscopes, track balls, touchpads, mouse, touch screens, or sensory gloves. Electronic controller 28 controls the movement of the segmented automatically controlled proximal portion 16, if present, of elongate body 12. Electronic controller 28 may be implemented using a motion control program running on a microcomputer or using an application-specific motion controller as will be appreciated by the skilled artisan. Alternatively, electronic controller, 28 may be implemented using, e.g., a neural network controller.

The actuators applying force to tendons which articulate steerable distal portion 14 and, in the embodiment, automatically controlled portion 16, may be included in electronic controller 28, as shown, or may be located separately and connected by a control cable. The tendons controlling steerable distal portion 14 and, in this embodiment, controllable segments 26 of automatically controlled portion 16, extend down the length of elongate body 12 and connect to the actuators. FIG. 1 shows a variation in which the tendons pass through handle 30 and connect directly to electronic controller 28 via quick-release connector 29. In this variation, the tendons are part of controller cable 42, although they could independently connect to the actuators, so long as the actuators are in communication with electronic controller 28. Alternatively, the tendons connected to steerable distal portion 16 could be connected to a manual actuation system comprising a knob/gear system, as in endoscopes sold by Olympus, Fujinon or Pentax. Other variations of connecting tendons 78 to the actuators are more thoroughly discussed in U.S. patent application Ser. No. 10/988,212, which is incorporated in its entirety herein by reference.

An Axial motion transducer (also called a depth referencing device or datum) 48 may be provided for measuring the axial motion, i.e., the depth change of elongate body 12 as it is advanced and withdrawn. As elongate body 12 of endoscope 10 slides through axial motion transducer 48, it indicates the axial position of the elongate body 12 with respect to a fixed point of reference. Axial motion transducer 48 is more fully described in U.S. patent application Ser. No. 10/229,577 previously incorporated herein by reference.

Figure 2:
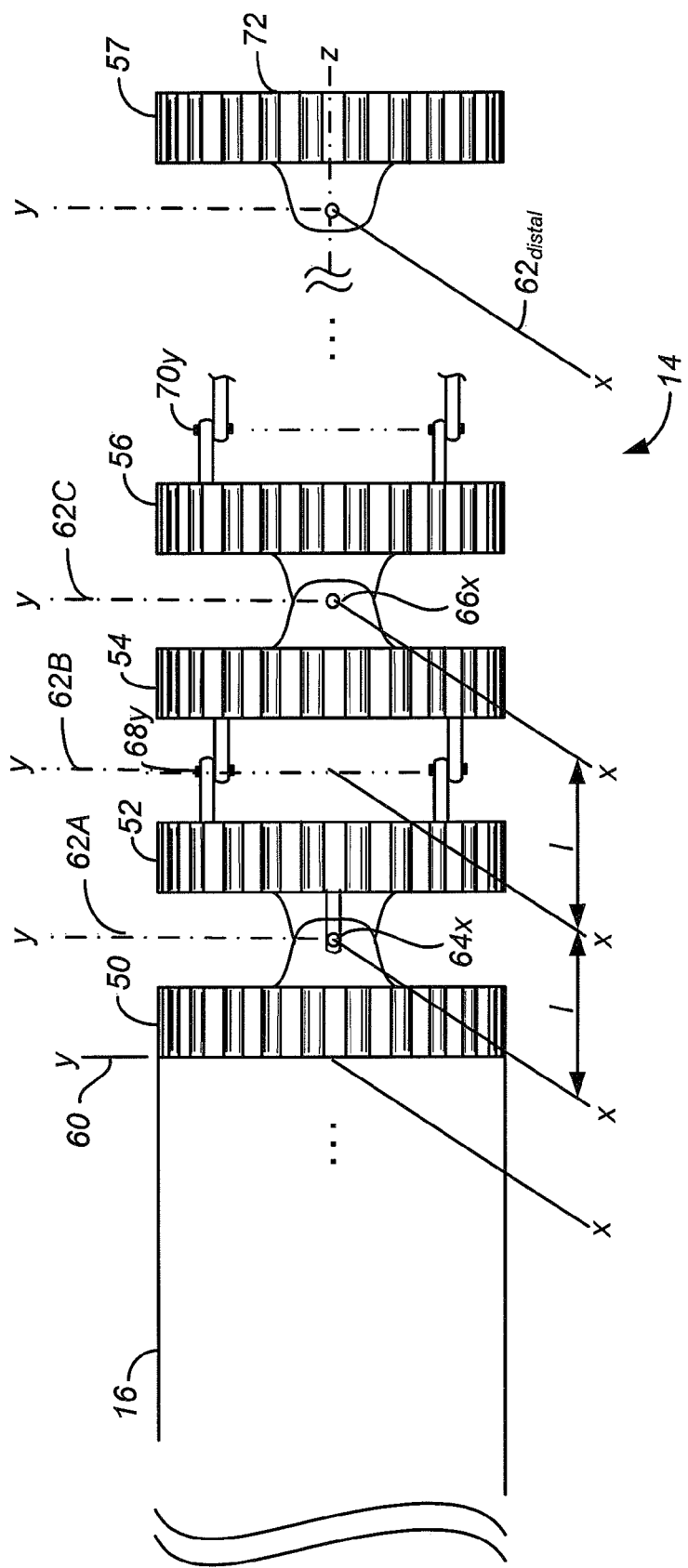
FIG. 2 depicts several joint segments of a steerable distal portion of an endoscope in accordance with an embodiment of the present invention.

Referring to FIG. 2, steerable distal portion 14 is preferably constructed from a plurality of joint segments 50, 52, 54, 56, 57, with only five shown in this example for the sake of clarity. The skilled artisan will readily recognize that any number of joint segments may be used, the ultimate number being primarily defined by the purpose for which steerable distal portion 14 will be used. Each joint segment has two joints, e.g., 64X and 64Y. The skilled artisan will appreciate that joint segments, as used herein, can also be referred as a link, where a link connects one joint to an adjacent joint. Steerable distal portion 14 is depicted in a straight configuration in z-y-x reference frame 60, which reference frame is preferably associated with the most proximal joint segment 50. The skilled artisan will recognize that each joint along the length of steerable distal portion 14 is associated with a z-y-x coordinate frame 62A, 62B . . . $62_{distal}$) and that z-y-x coordinate frame 62A for the most proximal joint 64X is preferably the same as a parallel to z-y-x reference frame 60. When steerable distal portion 14 is in the approximately straight configuration, as show in FIG. 2, the z-axis for z-y-x reference frame 60 and the z-axis for the z-y-x coordinate frames 62A, 62B, 62C . . . $62_{distal}$ are approximately the same, and the x-y planes are approximately parallel and spaced apart approximately by length l.

As show in FIG. 2, each joint segment 50, 52, 54, 56, 57 (with others omitted for clarity) has two joints, an x-joint 64X, 66X, and a y-joint 68Y, 70Y. The x-axis of each coordinate frame 62 runs approximately through or approximately parallel to x-joints 64X, 66X, and similarly the y-axis of each coordinate frame 62 runs approximately through or approximately parallel to the y-joint 68Y, 70Y. Joint segments 50, 52, 54, 56, 57 are alternately connected at y-joints and x-joints. Each joint segment, in this embodiment, can move with two degrees of freedom relative to an adjacent joint segment.

For example and not by way of limitation, FIG. 2 depicts four joint segments 50, 52, 54 56 and 57. In this example, left most joint segment 50 is the most proximal joint segment of steerable distal portion 14 and adjoins to the most distal portion of automatically controlled section 16 of endoscope 10. Z-Y-X reference frame 60 is located approximately at this junction, or thereabouts, such that steerable distal portion 14 bends relative to z-y-x reference frame 60. As described above, each joint (of which there are two) for each joint segment is associated with a z-y-x coordinate frame 62. It is noted, however, that the most proximal joint segment 50 has only one joint for the purposes of this example. In those joints, e.g., 64X and 66X in this example, where the x-axis runs through the joint, the joint segment 52 and 56 distal to that x-joint can rotate about the x-axis running through the joints 64X and 66X. Thus, in the example given, joint segment 52 can rotate about the x-axis running through joint 64X, thereby moving joint segment 52 up or down in the plane of the page or in the z-y plane of z-y-x coordinate frame 62A. Further, in the example given, joint segment 54 can rotate about y-axis running through joint 68Y, thereby moving joint segment 54 in and out of the plane of the page, or left and right in the z-x plane of the z-y-x coordinate frame 62B. Further details of this vertebra-type structure, and how it is assembled are provided in U.S. patent application Ser. No. 10/229,577, previously incorporated herein in its entirety.

Each of these rotations, whether about the y- or x-axis of the various coordinate frames 62, results in a rotation of coordinate frames 62 in three-dimensional space relative to each other and relative to reference frame 60. The rotation of the coordinate frames 62 can be represented using matrices, referred to as rotational matrices. John Craig, Introduction to Robotics 19-60 (2d Ed. 1986). Assuming the overall bend is approximately equally distributed to each joint segment across the length of steerable distal portion 14, Craig show that multiplication of the rotational matrices for coordinate frames 62 of the most distal joint 57 (which coordinate frame $62_{distal}$ is adjacent to or includes distal tip 72) to the most proximal joint 64X (which coordinate frame 62A is the same as, or at least parallel to reference frame 60) results in an overall rotational matrix describing rotation of the most distal coordinate frame $62_{distal}$ relative to the most proximal coordinate frame 62A and/or z-y-x reference frame 60.

Figure 3A:
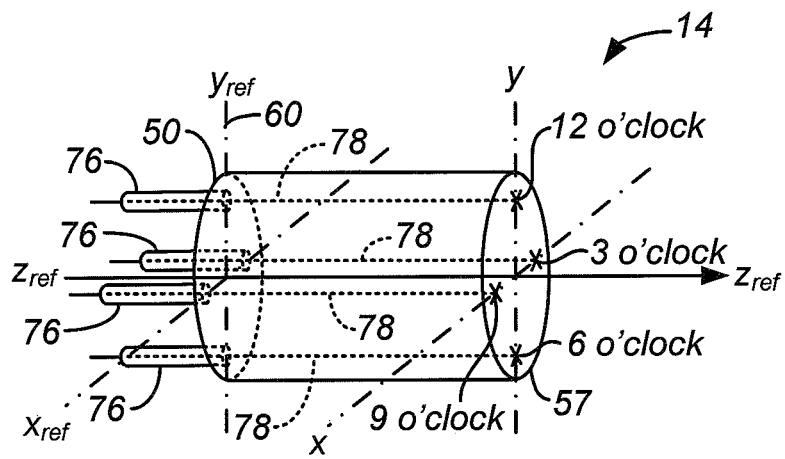
FIGS. 3A, 3B, and 3C depict three-dimensional views for describing articulation of the steerable distal portion of an endoscope in accordance with an embodiment of the present invention.
Figure 3B:
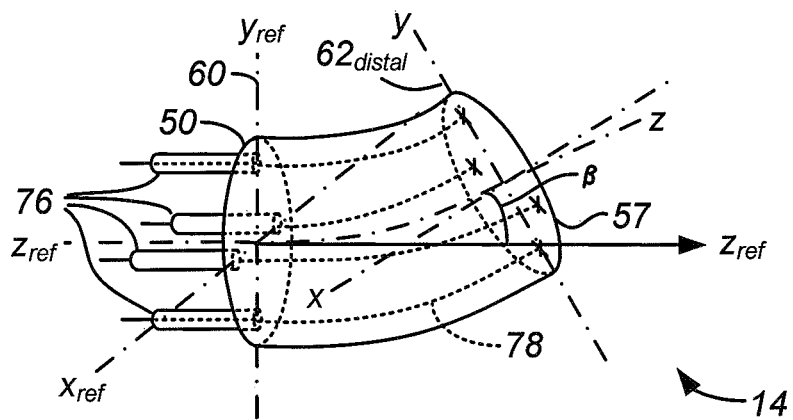
Figure 3C:
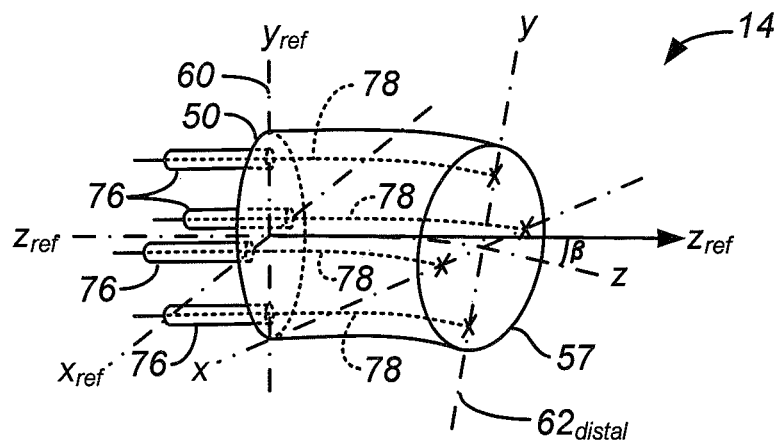

Referring now to FIG. 3 a schematic diagram of steerable distal portion 14 is provided for discussion purposes and to explain a preferred system and method for bending steerable distal portion 14. It is noted that details relating to the joint segments, joints and the interconnections of the joint segments have been eliminated from this figure for the sake of clarity. It is further noted that FIG. 3 is a good representation of the mathematical model where the overall rotation matrix discussed above describes the rotation of the most distal z-y-x coordinate frame $62_{distal}$ relative to the most proximal z-y-x coordinate frame 62A or alternatively reference frame 60. FIG. 3A shows a three-dimensional view of steerable distal portion in its substantially straight configuration. The most distal joint segment and the most proximal joint segment of steerable distal portion 14 are depicted as circles. Bowden-type cables extend down the length of elongate body 12 (not shown in FIG. 3A) and comprise coil tube 76 and tendons 78. Coil tube 76 house tendons 78 along the length of elongate body 12 (not shown in FIG. 3A), but not along the length of steerable distal portion 14. In the variation depicted in FIGS. 3A-C, four tendons 78 are depicted to articulate steerable distal portion 14. Bowden-type cable can be used to apply either tensile or compressive forces, i.e., they may be pushed or pulled, to articulate steerable distal portion 14 and can be actuated remotely to deliver forces as desired to bend steerable distal portion 14. In the present embodiment tendon 78 is fixed at the most distal joint segment 57 of steerable distal portion 14 and coil tube 76 is fixed at the proximal most joint segment 50 of steerable distal portion 14. In this manner, actuation of one or more tendons 78 causes steerable distal portion 14 to articulate.

In the variation depicted in FIG. 3A-C, four tendons are used to bend steerable distal portion 14, although more or fewer tendons could be used. Four tendons can reliably articulate steerable distal portion 14 in any direction without having to rotate steerable distal portion 14 or elongate body 12 about it longitudinal axis. Tendons 78 are preferably attached at the most distal joint segment 57 close to the edge of the joint segment, spaced equally apart, preferably and only by way of explanation at 12, 3, 6, and 9 O'clock.

FIG. 3A shows steerable distal portion 14 in its substantially straight configuration with four tendons 78 attached to distal most joint segment $57_{distal}$ as described above. As described above, tendons 78 are attached at their proximal ends to actuators (not shown in this figure), which places the tendon under tension or releases tension, thereby bending steerable distal portion 14. FIGS. 3B-C show steerable distal portion 14 bent by independently pulling or slacking each of the four tendons 78.

For example, referring to FIG. 3B, pulling on tendon 78 at the 12 O'clock position and easing tension on tendon 78 at the 6 O'clock position causes steerable distal portion 14 to bend in the positive y-direction with respect to the z-y-x reference frame 60. It is noted that the most distal z-y-x coordinate frame $62_{distal}$ rotates with respect to the z-y-x reference frame 60 and that β is the degree of overall bend of steerable distal portion 14. In this situation β is only along the positive y-axis, up, because only the tendon 78 at the 12 O'clock position was pulled while easing tension or giving slack to tendon 78 at 6 O'clock. The tendons 78 at three- and 9 O'clock were left substantially static in this example, and, thus, had approximately no or little affect on the overall bend of steerable distal portion 14. The reverse situation (not depicted), pulling on tendon 78 at the 6 O'clock position and slacking or easing the tension on tendon 78 at the 12 O'clock position will result in an overall bend of steerable distal portion 14 in the negative y-direction, or down. Referring to FIG. 3C the same logic applies to bend steerable distal portion 14 in the positive x-direction, right, by an overall bend angle of B, or a negative x-direction (not show), left. Steerable distal portion 14 can be bent in any direction by applying varying tensions to the tendons of axis, e.g., applying tension to the tendons at 12 O'clock and 2 O'clock result in an overall ben β up and to the left.

When tension applied to tendons 78 results in an overall bend of steerable distal portion 14 in the y-direction only, this is referred to as a y-bend. Similarly, when tension applied to tendons 78 results in an overall bend of steerable distal portion 14 in the x-direction only, this is referred to as an x-bend. The skilled artisan will also appreciate that the over bend β resulting from simultaneous y- and x-bends will have y- and x-components. The skilled artisan can determine the amount of length change of tendons 78 to achieve various y- and x-bends, by, for example and without limitation, examining the overall bend of steerable distal portion for various length changes. The amount of length change of tendons 78 that results in various observed x- and y-bends is also referred to herein as pull-distance. Alternatively, the skilled artisan could determine that the amount of tension required on tendons 78 to achieve the various y- and x-bends, again, by observing the over bend for the various tensions.

Figure 4:
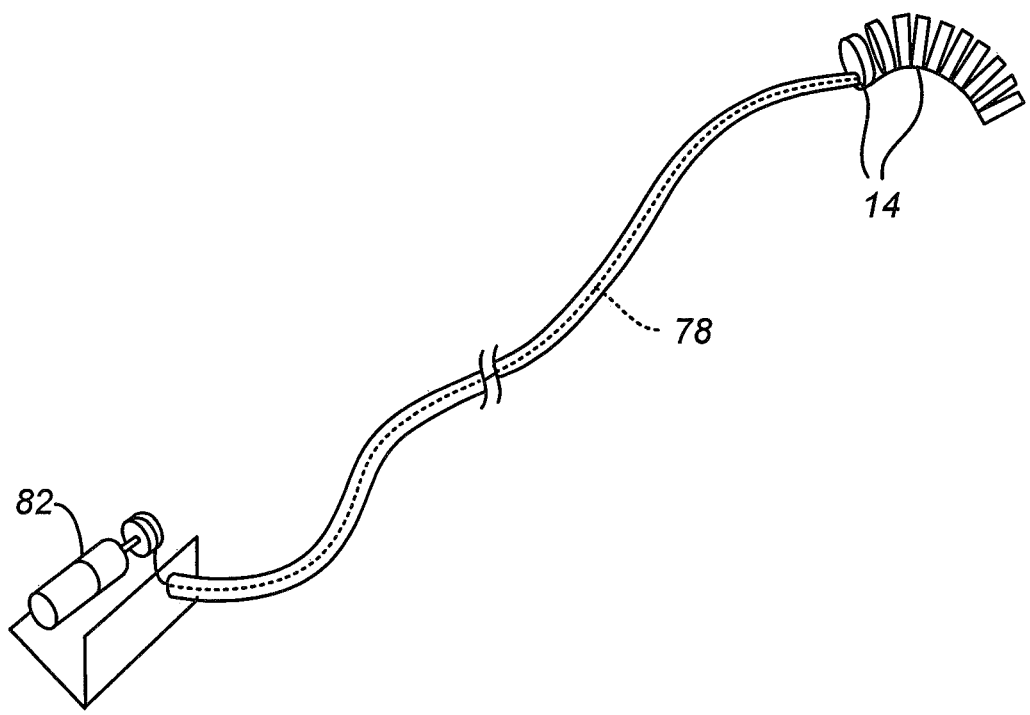
FIG. 4 depicts an actuator and tendon to articulate the steerable distal portion of an endoscope in accordance with an embodiment of the present invention.

For example, and without limitation, FIG. 4 shows a partial schematic representation of a single tendon 78 bending steerable distal portion 14. For clarity, the other parts of a complete endoscope have been omitted from FIG. 4. Tension applied to tendon 78 is transferred across the entire length of steerable distal portion 14 resulting in bending, as described above. Tendon 78 is placed in tension of actuator 82, which is shown, in this variation, as a motor pulling on tendon 78. In this embodiment the skilled artisan would determine the pull-distance applied by actuator 82 required to achieve a range of y-bends and x-bends can of steerable distal portion 14. Alternatively, tensions of tendon 78 to achieve an x- or y-bend can be determined or measured. The skilled artisan will recognize that factors, such as but not limited to, the amount of articulation along the length of body 12 and friction within coil pipes 76 will affect the amount of tension or pull-distance required to bend steerable distal portion 14. As another alternative, a sensor capable of measuring the x-bend, y-bend and/or overall bend could be placed on each joint segment of steerable distal portion 14 or along the length of steerable distal portion 14. The sensor then would report the x-bend, y-bend and/or overall bend of steerable distal portion 14 via a communication cable (optical fiber or wire) or wirelessly back to electronic controller 28. For example, and without limitation, a strain sensor could be placed along the length of steerable distal portion 14, wherein the amount of strain is indicative of the amount of bend the sensor, and therefor steerable distal portion 14, experiences.

A preferred embodiment of the present invention utilizes one actuator per tendon, and utilizes four tendons as described above. As described above, steering controller 44 is used to direct the actuators to apply tension to individual tendons depending where the user wants to steer the steerable distal portion 14. As also described above, tension in the overall bend, B, of steerable distal portion 14 is the approximate angle between the z-axis of z-y-x reference frame 60 and the z-axis of the most distal z-y-x coordinate frame $62_{distal}$. As described above, overall bend β and y-bend or x-bend are the same when either x-bend or y-bend is zero, respectively. The skilled artisan will appreciate that in this manner a user or the electronic controller 28 can determine the x- and y-bend or steerable distal portion 14, and, as described above, the overall bend. Further details of how to determine the x- and y-bend of steerable distal portion 14 are disclosed in U.S. patent application Ser. No. 11/603,943, incorporated herein it its entirety by reference. Alternatively, it will be recognized that fewer than fewer than four tensioning members may be used to articulate steerable distal portion 14, one for example as in a steerable arterial catheter.

As discussed above, Craig describes how to solve for an overall rotational matrix describing the rotation between z-y-x reference frame 60 and the most distal z-y-x coordinate frame $62_{distal}$. From this overall rotational matrix one can solve for the overall bend by equating the overall rotational matrix to the ZYZ Euler rotational matrix, and then solving to obtain the overall bend angle β, where the Euler rotational matrix is described in Craig. However, if steerable distal portion 14 comprising 21 joint segments (for example and not by way of limitation) were used, this would require multiplication of 21 matrices for each calculation of the overall bend. The skilled artisan will appreciate that this computation would require relatively significant computer time.

Figure 5A:
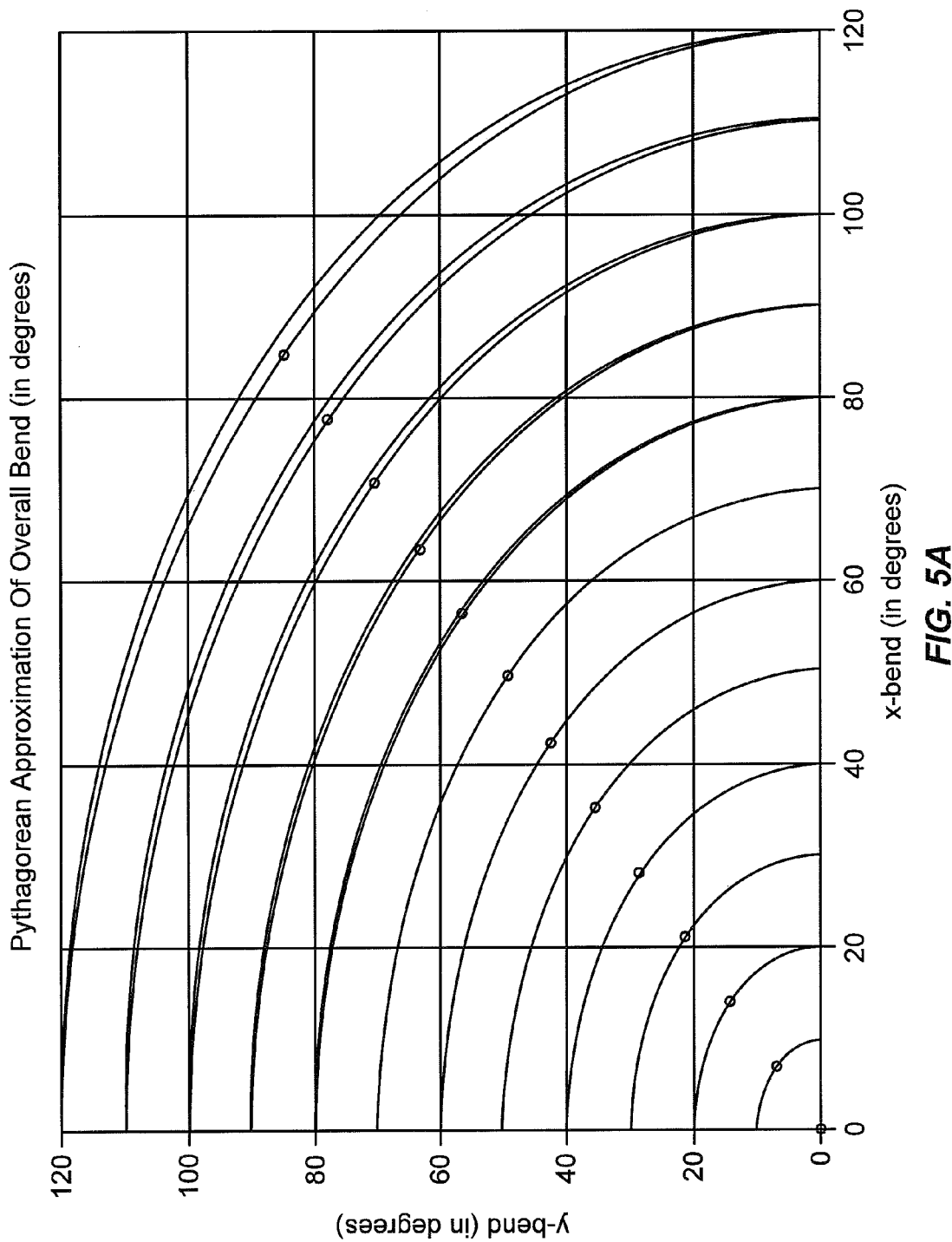
FIGS. 5A and 5B respectively show plots of the overall bend for an 8 joint-segment and a 21 joint-segment steerable distal portion of an endoscope with relation to a Pythagorean approximation of the overall bend for the 8 joint-segment and 21 joint-segment steerable distal portions.
Figure 5B:
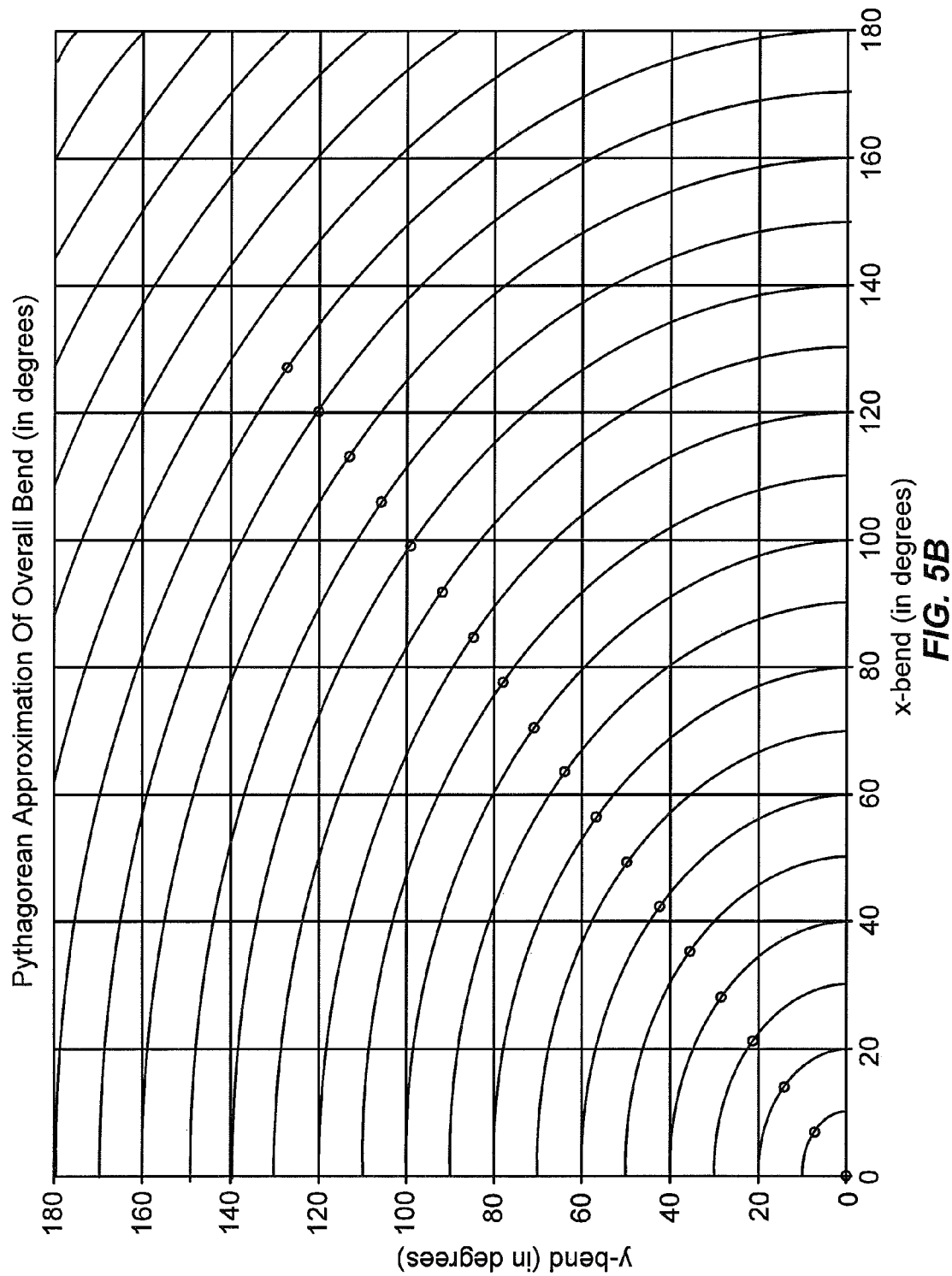

Referring to FIG. 5A-B, the Pythagorean Theorem provides a very good approximation of the overall bend angle. FIG. 5A shows a plot of the overall bend resulting from a y-bend and an x-bend, and a plot for $\sqrt{(y\text{-bend})^2+(x\text{-bend})^2}$, the latter plot being identified by open circles "o", at which points the y-bend equals the x-bend. FIG. 5A is a plot for steerable distal portion 14 comprising 11 joint segments and FIG. 5B is a plot for steerable distal portion 14 comprising 22 joint segments. The 11- and 22-joint segments are used as examples and not by way of limitation. The skilled artisan will appreciate that more or fewer joint segments may be utilized. Both FIGS. 5A-B establish that the Pythagorean sum of the y-bend and x-bend angles approximates the overall bend of steerable distal portion 14. The y-bend and x-bend will also approximate the amount of bend in the y- and x-directions in the z-y-x reference frame 60, which provides the approximate up-, down-, left- and right-direction of steerable distal portion in relation to the origin of the z-y-x reference frame 60. This Pythagorean approximation substantially eases the computational load, and greatly facilitates plotting the overall bend and x-bend and y-bend. However, the skilled artisan will appreciate the process can be accomplished computationally by multiplying out the individual rotational matrices.

Figure 6:
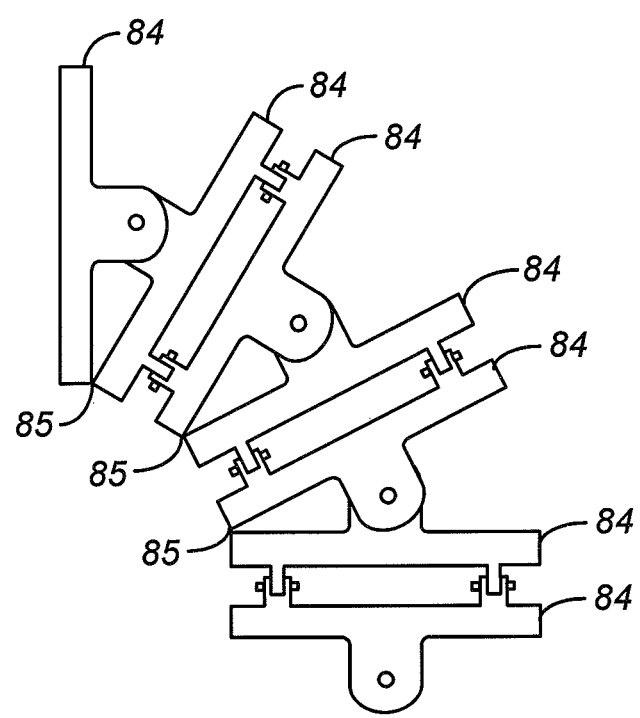
FIG. 6 depicts a plurality of joint segments of a steerable distal portion for illustration of hard-stops.

It is noted that the Pythagorean sum approximation of FIG. 5A with 8 joint segments is not quite as good as the approximation of FIG. 5B with 21 joint segments. Considering FIG. 6, joint segments 84 have a limited range of motion about either the y-axis or x-axis of rotation; each of the joint segments has a hard-stop 85 beyond which no more rotation about the y- or x-axis is physically possible. It is with multiple joint segments 84 that steerable distal portion 14 can achieve overall bend angles much greater than any individual angle of deflection achievable to one joint segment 84 about its y- or x-joint axis. Nevertheless, as a result of the physical hard stops of individual joint segments 84, a multi-joint segment steerable distal portion 14 has physical outer limits or hard stops beyond which it will not bend. As the number of segments in steerable distal portion increases, as in FIG. 5B relative to FIG. 5A, the cumulative bend of the joint segments become more continuous, thereby making the approximation even better.

As appreciated by the skilled artisan, a user will insert and attempt to guide an endoscope to a remote location using a video image to visualize where the endoscope is going, using steerable distal portion 14 to guide the user around any obstacles visualized, and then advancing the endoscope. However, as a skilled artisan will also appreciate, and as described above, a user can become easily disoriented as to the orientation of steerable distal portion 14, even with live video feed from the camera.

Referring to FIG. 7, one variation of the present invention provides a monitor 86 having a unique graphical user interface (GUI) including a bull's-eye positioning aid 88 for steerable distal portion 14. Bull's-eye positioning aid 88, I this embodiment, comprises two concentric circles 90A-B, with cross-hair 92 through the approximate center of concentric circles 90A-B. The skilled artisan will appreciate that concentric circles may take on any shape defined by the user, for examples ovals, squares, rectangles or any shape desired by the skilled artisan to convey the orientation information to the user. The distance away from the intersection of cross-hair 92 is approximately the degree of overall bend of steerable distal portion 14. Concentric circles 90A-B represent an amount of overall bend of steerable distal portion 14 (90 and 180 degrees in this example), horizontal axis 94 of cross-hair 92 represents the x-bend or left/right orientation, and vertical axis 96 of cross-hair 92 represents the y-bend or up/down orientation. Horizontal and vertical axes of cross-hair 92, in this embodiment, are divided linearly into degrees of deflection. Icon 98, here a dot, represents a vector diagram. The skilled artisan will appreciate that icon 98 can have any shape, and is simply a graphic representation graphically representing the orientation information for steerable distal portion 14. If icon 98 is centered on cross-hair 92 as shown in FIG. 7A, steerable distal portion 14 is in its approximately straight, looking forward configuration. The skilled artisan will appreciate that monitor 86 may also display useful information other than the GUI in accordance with an embodiment of the present invention. For example, and without limitation, monitor 86 may also display video images from camera 24 or a three-dimensional shape of the entire endoscope. The skilled artisan will further appreciate that indicators other than the cross-hair may be used to represent the orientation of steerable distal portion 14. For example, and without limitation, other shapes not at right angles may be used, polar coordinates may be used, logarithmic scales and coordinates may be used; the skilled artisan can use any indicator that conveniently displays the orientation of steerable distal portion 14, even a tabular list of bend and overall angles.

Figure 7A:
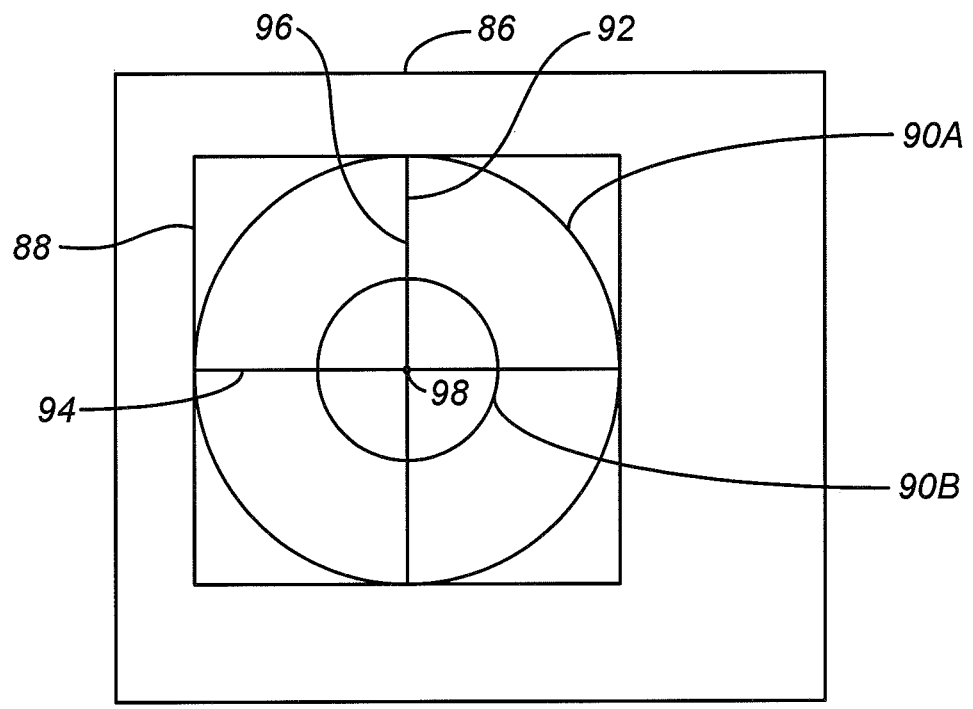
FIGS. 7A, 7B, 7C, and 7D depict a graphical user interface in accordance with an embodiment of the present invention.
Figure 7B:
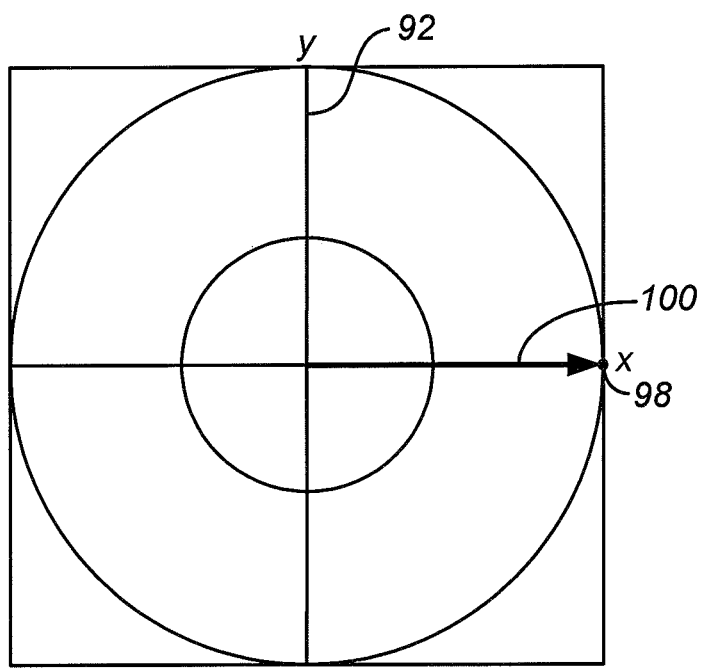
Figure 7C:
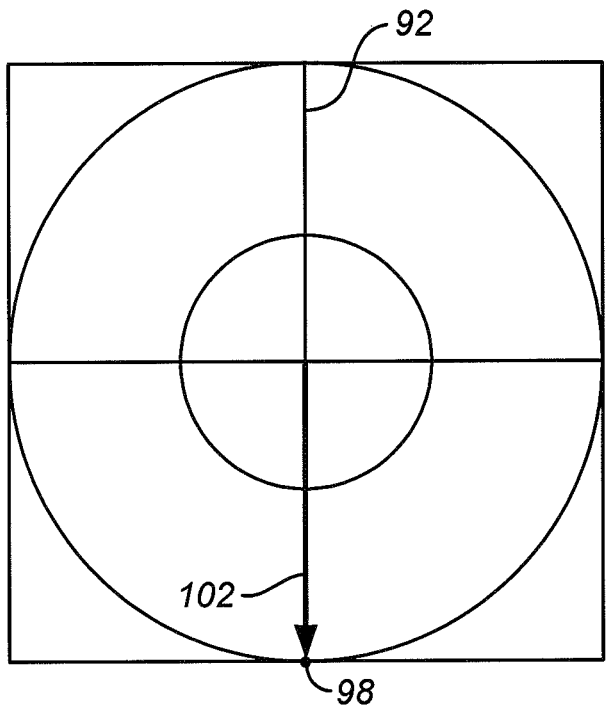
Figure 7D:
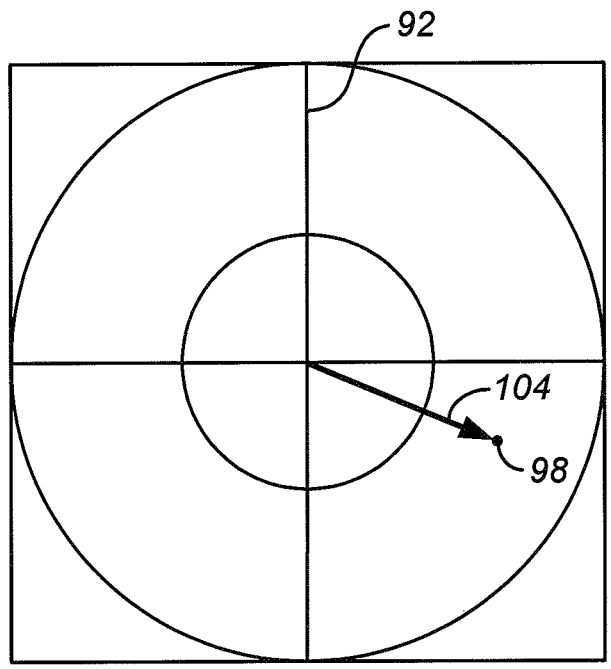

FIGS. 7B-D provide examples of how to use an embodiment of the GUI of the present invention. in FIG. 7A, icon 98 is centered on cross-hair 92, and, therefore, steerable distal portion 14 is in an approximate straight ahead position, as depicted in the three-dimensional diagram of steerable distal portion 14 in FIG. 3A. In FIG. 7B, icon 98 is located on 180 degree circle; this, the magnitude of vector 100 from the origin of cross-hair 92 to icon 98 is 180 degrees. The x-bend in FIG. 7B is also 180 degrees right and the y-bend is zero. Therefore, the overall bend is 180 degrees to the left, like the user is looking directly behind her over the right shoulder. FIG. 7C shows icon 98 having a vector 102 with a magnitude of 180 degrees, but this time with a y-bend 180 degrees down and the x-bend us zero, FIG. 7D shows icon 98 having vector 104 with a y-bend component of approximately 45 degrees down, and an x-bend component of approximately 135 degrees to the right. The magnitude of vector 104, or overall bend, is approximately $\sqrt{(45)^2+(135)^2}$ or approximately 142 degrees. Therefore, the user has steerable distal portion directed approximately 45 degrees down and approximately 135 degrees to the right with an overall bend of approximately 142 degrees, as depicted in FIG. 7D.

Alternatively, the y-bend, x-bend and overall bend could be depicted as a three dimensional object on a two-dimensional display (not shown). In this alternative embodiment, a three dimensional object of steerable distal portion 14 is graphically displayed on the GUI. This can be done in many different ways, for example in shadow, or using shading and colors to provide a more realistic three dimensional representation. The x-bend, y-bend and over all bend can then be represented by changing the three-dimensional representation on the GUI. The shape of the steerable distal portion can be shown relative to the distal end of the proximal portion. The distal end of the proximal portion is, preferably though not exclusively, represented at approximately a 45 degree angle relative to the screen of the GUI. This will provide the user of good view of the three-dimensional orientation of the steerable distal portion as the shape of this portion is changed by the user's direction. As the skilled artisan will appreciate the y-bend, x-bend and overall bend information can be used to generate such a three-dimensional object on a graphical user interface such that the endoscope user can visually see the approximate three-dimensional orientation of steerable distal portion 14 on the display. The skilled artisan will appreciated that the three-dimensional object need not be scaled to the size of steerable distal portion, although it could be. The three-dimensional object is manipulated using data from the y-bend, x-bend and overall bend to provide the user with a visual representation of the approximate 3-dimensional orientation of steerable distal portion 14 while it is being manipulated by the user to examine remote locations, such as in a colonoscopy. It is noted, however, the preferred system and method of the present invention uses a dot-vector diagram with a cross-hair graphical user interface display, as previously described.

Figure 8:
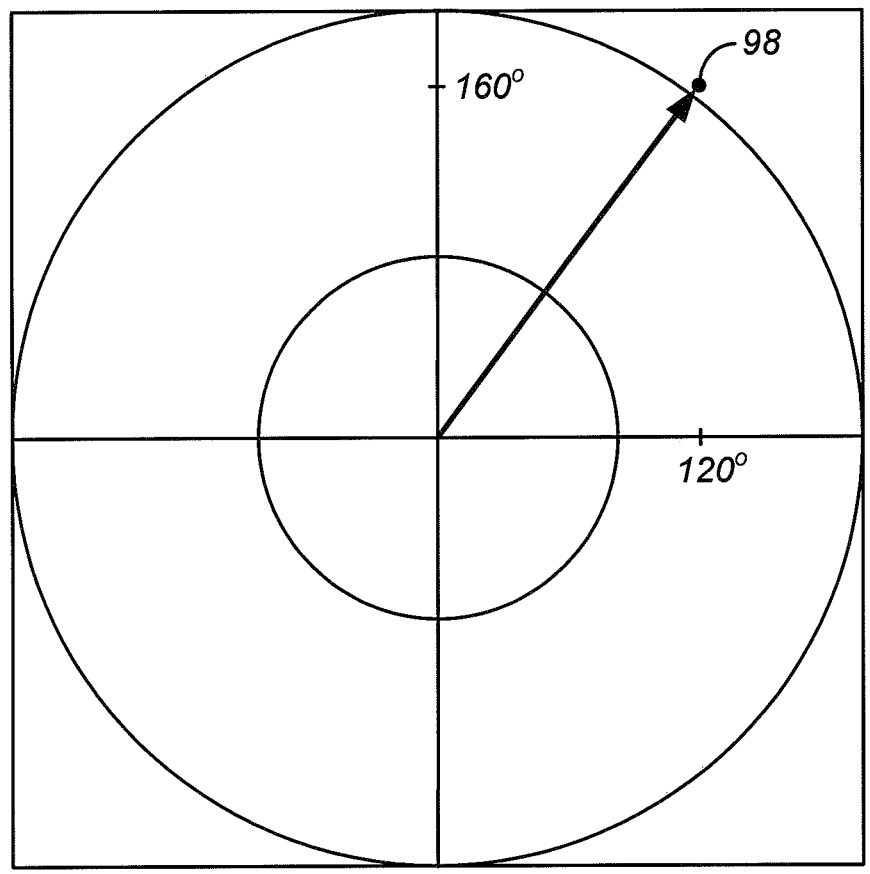
FIG. 8 depicts a non-limiting example of an over-saturated configuration as represented on a graphical user interface in accordance with an embodiment of the present invention.

As described above, hard stops of individual joint segments lead to steerable distal portion 14 having hard stops as well. In particular, if all the joint segments are rotated to their hard stops about the y-joint axis and not rotated at all about their x-joint axis and vice versa, this will result in a maximum bend or hard stop in the y- and x-directions respectively, i.e., steerable distal portion 14 can bend no further in that particular direction. This condition is referred to herein as saturated. While a multi-joint segment steerable distal portion may be saturated when bent only in the x- or y-direction, it can have a much greater overall bend when bent in the x- and y-directions simultaneously. FIG. 8 depicts an example where saturation in the y- and x-directions is 180 degrees. The example in FIG. 8 shows a y-bend up to 160 degrees and an x-bend right of 120 degrees that result in an approximate overall bend of 200 degrees up and to the right, where 200 degrees larger than the saturation bend in either the y- or x-directions, 180 degrees in this example. The skilled artisan will appreciate that the saturated bend in y- or x-directions do not have to be equal, and can be more or less than 180 degrees. An overall bend above the saturated y- or saturated x-direction is referred to herein as over-saturated.

Figure 9:
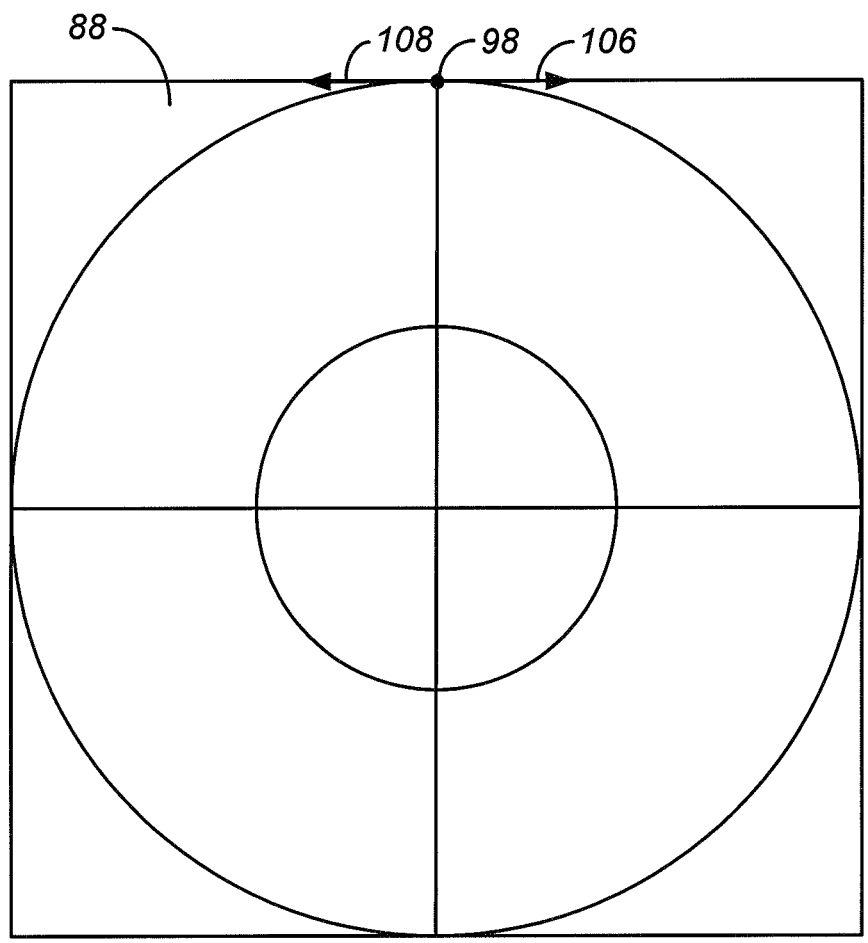
FIG. 9 illustrates limiting the overall bend to approximately 180 degrees in accordance with an embodiment of the present invention.

Referring to FIG. 9, when using the bull's-eye positioning aid 88, in accordance to one embodiment of the present invention, a user could try to steer left, right or down from the fully saturated up position, see icon 98. The user cannot steer up from the position represented by icon 98, as steerable distal portion 14 is at a hard stop for this direction in this particular example. If the user steers immediately right (as depicted by arrow 106), steerable distal portion 14 will begin to over-saturate, but the construction of steerable distal portion 14 will mechanically permit it to become over-saturated. In regions of over-saturation, the camera can move with substantial rotation as well as translation, which can result in substantially confusing camera motion for the use. In order to provide the user with smooth travel of the steerable distal portion 14 and the icon image thereof, an embodiment of the present invention limits the amount of overall bend to a preset amount. In the present example the maximum amount of the overall bend permitted is 180 degrees in any direction, although the skilled artisan will recognize that the other limits may be used, and these limits may depend on the physical limitations of the joint segments used to make steerable distal portion 14.

Figure 10:
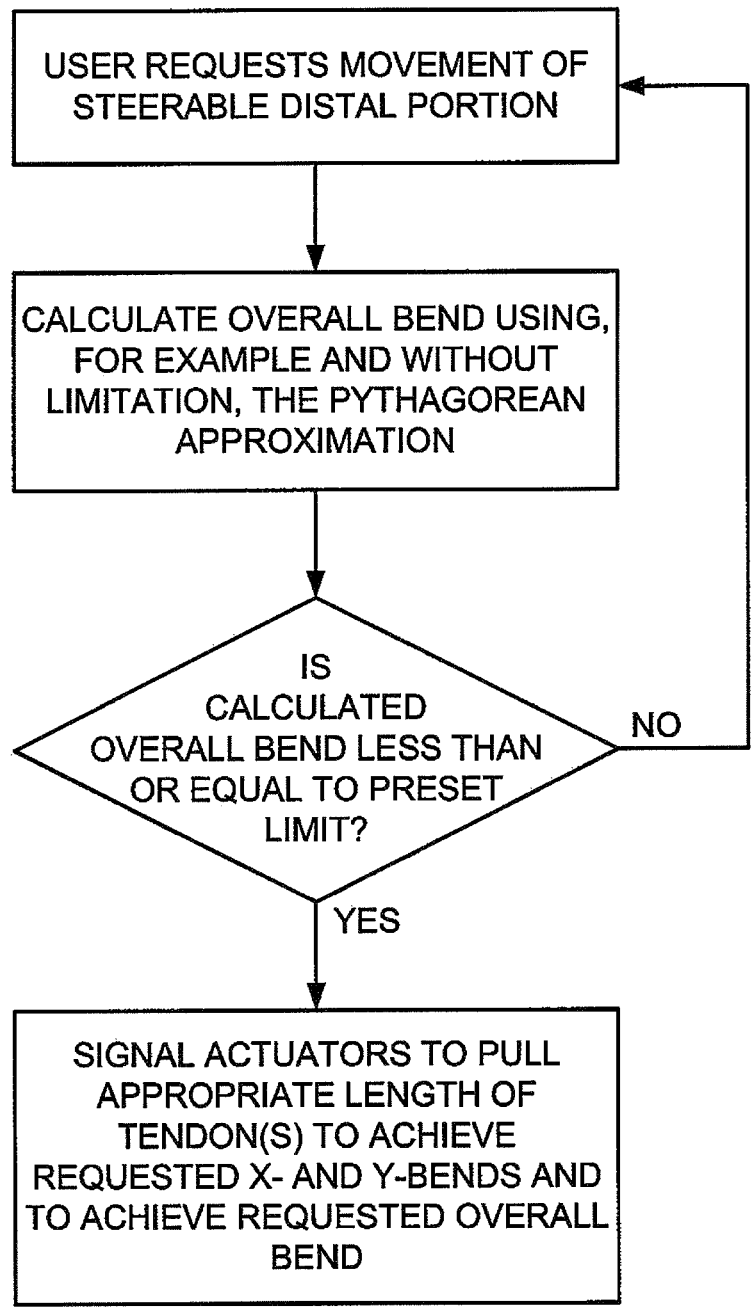
FIG. 10 is a flow chart depicting one embodiment of a method of preventing over-saturated orientation of an elongate instrument.

Referring to FIG. 10, in one embodiment of the present invention, the user requests a certain overall bend and direction by moving steering controller 44, e.g., a joy stick. Electronic controller 28 then calculates the overall bend that would result from the motion requested by the user via steering controller 44. A preferred embodiment of the present invention calculates the overall bend by the Pythagorean approximation using the requested x-bend and requested y-bend. As discussed above, electronic controller 28 has a memory of the y- and x-bend resulting from the amount of tension or pull-distance requested on the actuators. If the overall bend requested is less than or equal to the preset limit of the overall bend, 180 degrees in the present example, then the electronic controller 28 will signal the actuators to apply the appropriate tension to the tendons or pull the appropriate distance of the tendon to achieve the requested x- and y-bends. If the calculated overall bend is greater than the preset limit then the electronic controller will wait for the user to modify the requested movement, for example by moving the joystick in a slightly different direction, at which time the calculation and command instructions will start over. Alternatively, the electronic controller 28 could allow movement of steerable distal portion 14, but only up to the preset overall bend limit, 180 degrees in the example. The skilled artisan understands that other methods exist for electronic controller 28 to limit the overall bend of steerable distal portion 14 to a preset limit. In this manner the user will experience a smooth transition through a full range of motion.

The cross-hair and centered-is-straight concept allows a disoriented user to quickly and easily return to the steerable distal portion 14 to an approximately straight ahead condition. Bull's-eye positioning aid 88 of the present invention is particularly useful in helping a user who has become disoriented, for example after performing an inspection, providing therapy, or performing some procedure, to return the steerable distal portion 14 to a centered, forward looking condition to resume navigation of endoscope 10 further into the remote areas. Bull's-eye positioning aid 88 of the present invention provides a user with an easy to understand orientation of the steerable distal portion of endoscope 10 relative to a centered, forward looking condition similar to the way aircraft instruments display the attitude of an aircraft to an artificial horizon. In much the same way, bull's-eye positioning aid 88 helps the user maintain the attitude of steerable distal portion 14 of endoscope 10. The zero/zero attitude in the illustrative embodiment is the approximately straight orientation or center/forward orientation of steerable distal portion 14, but could be any other convenient orientation as will be appreciated by the skilled artisan. The appearance of the system used to visualize the orientation steerable distal portion 14 may also be changed to accommodate the user. For example and without limitation, more or less than two concentric circles may be used, and those used may be for any degrees of overall bend, as suits the user.

The foregoing description, for purposes of explanation, used some specific nomenclature to provide a thorough understanding of the invention. Nevertheless, the foregoing descriptions of the preferred embodiments of the present invention are presented for purposes of illustration and description and are not intended to be exhaustive or to limit the invention to the precise forms disclosed; obvious modifications and variations are possible in view of the above teachings. For example, and not be way of limitation, similar to the endoscope description above, tools of a robotically controlled surgical instrument also have a fixed point or points from which the tools articulate, and the user of such tools has the need to know the orientation of these tools while remotely working with the tools inside a body. Thus, the skilled artisan will appreciate the need to visualize the orientation of various surgical tools extending from a robotic surgical device or platform similar to the need to visualize the orientation of steerable distal portion 14 of an endoscope. Thus, the skilled artisan will appreciate that embodiments of the present invention can be either directly used for visualizing robotically controlled surgical instruments, or can be easily modified without going out of the bounds of the claimed invention to accomplish this purpose. It is intended that the scope of the invention be defined by the following claims and their equivalents.

What is claimed is:

1. A system for graphically visualizing an approximate overall bend of a steerable distal portion of an elongate instrument relative to an x-y-z reference frame, comprising:
    an instrument having an elongate body, said elongate body comprising a proximal portion and a steerable distal portion extending longitudinally along a z-axis of the reference frame when in an approximately straight position;
    at least one tensioning member attached to said steerable distal portion, wherein actuation of said at least one tensioning member results in an approximate y-bend and an approximate x-bend of said steerable distal portion, and wherein said approximate y-bend and approximate x-bend define the approximate overall bend of said steerable distal portion;
    a graphical user interface representing an x-y plane of the reference frame; and
    an icon displayed on the graphical user interface, the icon representing a magnitude and a direction of the approximate overall bend of the steerable distal portion
    wherein:
        an origin is defined on the graphical user interface, the origin corresponding to an intersection of the x-y plane and the z-axis;
        a distance between the icon and the origin corresponds to the magnitude of the approximate overall bend; and
        an orientation of the icon with reference to the origin corresponds to the direction of the approximate overall bend.

2. The system according to claim 1, wherein said graphical user interface further comprises an indicator, and wherein a location of said icon on said indicator relevant to a point of reference on said indicator represents the magnitude of said approximate overall bend.

3. The system according to claim 2, wherein said indicator comprises at least one oval.

4. The system according to claim 2, wherein said indicator comprises at least one square.

5. The system according to claim 1, wherein said graphical user interface further comprises an indicator, and wherein a location of said icon on said indicator relevant to a point of reference on said indicator represents the magnitude and direction of said approximate overall bend.

6. The system according to claim 5, wherein said indicator comprises a cross-hair, and wherein the location of said icon along a horizontal axis of said cross-hair represents said approximate x-bend and the location of said icon along a vertical axis of said cross-hair represents said approximate y-bend of said steerable distal portion.

7. The system according to claim 6, wherein an intersection of said cross-hair represents an the approximately straight position of said steerable distal portion.

8. The system according to claim 6, wherein a distance from a center of said cross-hair to said icon represents a degree of said approximate overall bend of said steerable distal portion.

9. The system according to claim 6, wherein said cross-hair extends through an approximate center of at least one non-circular shape.

10. The system according to claim 6, wherein said cross-hair extends through an approximate center of at least one circle.

11. The system according to claim 10, wherein said at least one circle comprises a plurality of concentric circles.

12. The system according to claim 11, wherein an inner circle of the concentric circles represents 90 degrees of the approximate overall bend and an outer circle of the concentric circles represents 180 degrees of the approximate overall bend of said steerable distal portion.

13. The system according to claim 1, wherein the origin represents a proximal end of the steerable distal portion.

14. The system according to claim 1, wherein the x-y-z reference frame comprises a Cartesian reference frame.

15. The system according to claim 1, wherein the icon is a single icon.

16. The system according to claim 1, wherein a plurality of pull-distances of the at least one tensioning member correlates to a plurality of bends in the x-z and y-z planes.

17. A system for graphically visualizing an approximate overall bend of a steerable distal portion of an elongate instrument relative to an x-y-z reference frame, comprising:

an instrument having an elongate body, said elongate body comprising a proximal portion and a steerable distal portion extending longitudinally along a z-axis of the reference frame when in an approximately straight position;

at least one tensioning member attached to said steerable distal portion, wherein actuation of said at least one tensioning member results in an approximate y-bend and an approximate x-bend of said steerable distal portion, and wherein said approximate y-bend and approximate x-bend define an approximate overall bend of said steerable distal portion;

a graphical user interface representing an x-y plane of the reference frame; and a vector diagram displayed on the graphical user interface, the vector diagram representing a magnitude and a direction of the approximate overall bend of the steerable distal portion, wherein:

an origin is defined on the graphical user interface, the origin corresponding to an intersection of the x-y plane and the z-axis;

a distance between at least a portion of the origin and an end of a vector of the vector diagram corresponds to the magnitude of the approximate overall bend; and an orientation of at least a portion of the vector with reference to the origin corresponds to the direction of the approximate overall bend.

18. The system according to claim 17, wherein a magnitude of a vector of the vector diagram represents the magnitude in degrees of the approximate overall bend.

19. The system according to claim 18, wherein a direction of the vector represents the direction of the approximate overall bend.

* * * * *